(12) United States Patent
Garber et al.

(10) Patent No.: US 12,340,898 B2
(45) Date of Patent: Jun. 24, 2025

(54) SYSTEM AND METHOD FOR DETERMINING CUSTOMER/PATIENT WAIT TIMES

(71) Applicant: Happy Patient LLC, Roslyn Heights, NY (US)

(72) Inventors: Shawn Garber, Brookville, NY (US); Justin Garber, Brookville, NY (US)

(73) Assignee: Happy Patient New York, LLC, Roslyn Heights, NY (US)

( * ) Notice: Subject to any disclaimer, the term of this patent is extended or adjusted under 35 U.S.C. 154(b) by 0 days.

(21) Appl. No.: 18/614,210

(22) Filed: Mar. 22, 2024

(65) Prior Publication Data

US 2024/0233929 A1    Jul. 11, 2024

Related U.S. Application Data

(63) Continuation of application No. 18/482,941, filed on Oct. 9, 2023.

(60) Provisional application No. 63/414,650, filed on Oct. 10, 2022.

(51) Int. Cl.
| | |
|---|---|
| *G16H 40/20* | (2018.01) |
| *G01S 5/02* | (2010.01) |
| *G16H 10/60* | (2018.01) |
| *G16H 50/20* | (2018.01) |
| *H04W 4/029* | (2018.01) |
| *H04W 4/80* | (2018.01) |

(52) U.S. Cl.
CPC .......... *G16H 40/20* (2018.01); *G01S 5/0231* (2013.01); *G16H 10/60* (2018.01); *G16H 50/20* (2018.01); *H04W 4/029* (2018.02); *H04W 4/80* (2018.02)

(58) Field of Classification Search
CPC ........ G16H 40/20; G16H 10/60; G16H 50/20; H04W 4/029; H04W 4/80; G01S 5/0231
USPC ......................................................... 705/2–3
See application file for complete search history.

(56) References Cited

U.S. PATENT DOCUMENTS

| | | | | |
|---|---|---|---|---|
| 10,318,968 | B2 * | 6/2019 | Tineo | H04W 4/06 |
| 10,373,170 | B2 * | 8/2019 | Baker | G06Q 30/0619 |
| 11,994,879 | B2 * | 5/2024 | Di Benedetto | B64U 80/25 |
| 2009/0252318 | A1 * | 10/2009 | Smith | H04M 3/5238 |
| | | | | 379/265.1 |
| 2014/0114807 | A1 * | 4/2014 | Baker | G06Q 30/0601 |
| | | | | 705/26.41 |
| 2015/0134374 | A1 * | 5/2015 | Schulz | G06Q 10/02 |
| | | | | 705/5 |
| 2016/0192149 | A1 * | 6/2016 | Zises | H04W 4/027 |
| | | | | 455/456.3 |
| 2017/0124526 | A1 * | 5/2017 | Sanderford | G06Q 10/1095 |
| 2017/0352043 | A1 * | 12/2017 | Tineo | H04W 4/027 |
| 2019/0066087 | A1 * | 2/2019 | Shayovitz | G06Q 20/20 |
| 2021/0097524 | A1 * | 4/2021 | Shayovitz | G06Q 10/06 |

(Continued)

*Primary Examiner* — Michael Tomaszewski
(74) *Attorney, Agent, or Firm* — White and Williams, LLP

(57) ABSTRACT

The present invention is directed to the field of Bluetooth Low Energy ("BLE") enabled mobile device applications and, specifically, to a mobile device application that allows a customer or patient to view their actual wait time to see a doctor or other service provider. The present invention determines actual wait times based on the patients and providers within range of BLE beacons that are located in every room of an office space or other indoor area. An algorithm analyzes the real-time location data of in-office staff and patients to notify incoming patients of actual wait times.

23 Claims, 35 Drawing Sheets

(56) References Cited

U.S. PATENT DOCUMENTS

2024/0145076 A1* 5/2024 Garber .................. G16H 50/20
2024/0233929 A1* 7/2024 Garber ............... G06Q 10/1093

* cited by examiner

ROBUST REPORTING SYSTEM

Settings for New York Bariatric Group

Offices | Time Zone | Location | Notifications | Scheduling | EMR

Minimum seconds in room
[ 12                seconds ] ⓘ

Minimum number of consecutive pings
[ 2 ] ⓘ

Weak signal floor
[ -90                  dBm ] ⓘ

Max signal ceiling
[ 0                    dBm ] ⓘ

Ranging timeout
[ 1                minutes ] ⓘ

Minutes after checkout to stop tracking
[ 2                minutes ] ⓘ

Minutes after no ranging to checkout
[ 5                minutes ] ⓘ

[ Save ]

FIGURE 8

| PracticeName | OfficeName | RoomName | avg_median_d | num_pings | last_ping |
|---|---|---|---|---|---|
| New York Bariatric Group | Roslyn | Exam 1 | -87.0 | 10 | 2023-02-09 13:40:16.847 |
| New York Bariatric Group | Roslyn | Exam 2 | -95.43014705882354 | 272 | 2023-02-08 22:17:42.722 |
| New York Bariatric Group | Roslyn | Reception | -64.7 | 10 | 2023-02-09 13:40:24.148 |
| New York Bariatric Group | Westchester | Exam 1 | -49.88028169014085 | 284 | 2023-02-08 22:17:42.722 |
| New York Bariatric Group | Westchester | Exam 2 | -93.46808510638297 | 282 | 2023-02-08 22:17:33.744 |
| New York Bariatric Group | Westchester | Exam 3 | -83.78521136760563 | 284 | 2023-02-08 22:17:42.722 |
| New York Bariatric Group | Westchester | Reception | -48.65 | 20 | 2023-02-08 20:41:56.691 |

FIGURE 9

Settings for New York Bariatric Group

Offices    Time Zone    Location    Notifications    Scheduling    EMR

Patient prep time
[ 5 ] minutes

Patient in room buffer
[ 15 ] minutes

Provider delay considered late
[ 5 ] minutes

Minimum patient notice before appointment schedule shift
[ 60 ] minutes

Appointment Status Types:

scheduled — Scheduled
onTime — On Time
delayed — Delayed
patientCheckedIn — Patient Checked In
patientInRoom — Patient in Room
inProgress — In Progress
reScheduled — Rescheduled
canceled — Canceled
completed — Completed

Action Level

Action Needed
- Patient in Room
- Delayed
- Canceled

Followup Needed
- Patient Checked In
- In Progress

No Action Needed
- Scheduled
- On Time
- Rescheduled
- Completed

Patient Status Types:

InOffice
InWaitingRoom
TakenToRoom
InRoomAlone
InRoomWithProvider
InRoomWithStaff
InRoomWithProviderAndStaff
InCheckoutArea
LeftOffice

Room Status:

Available
Appointment
PatientWaiting
Needs Reset

Room Types:

Checkin
Checkout
DocsOffice
Exam
Other

FIGURE 12B

SYSTEM AND METHOD FOR DETERMINING CUSTOMER/PATIENT WAIT TIMES

CROSS REFERENCE TO RELATED APPLICATIONS

This application is a continuation of U.S. patent application Ser. No. 18/482,941, filed Oct. 19, 2023, which claims the benefit of U.S. Provisional Application Ser. No. 63/414,650, filed on Oct. 10, 2022, the contents of which are incorporated herein.

BACKGROUND

Doctors and other healthcare providers are typically very busy. Doctors and other healthcare providers who work on an appointment-basis can frequently become overwhelmed by a combination of unscheduled walk-in patients, late arriving patients, no-shows, appointment overruns, staff shortages, and other factors.

When the above factors occur, their combined effect can cause patient wait times to increase dramatically, even for patients with scheduled appointments. The vast majority of patients dislike these extensive wait times and as a result, service providers must attempt to reduce wait times or communicate the changes in wait times to the prospective patients. Mobile device applications have been developed to allow patients to view service wait times, schedule appointments, and receive other information. However, the wait times reported in these existing applications are estimations made by patients or otherwise determined by manual inputs provided by the office staff.

SUMMARY

The present invention is directed to a mobile device application for measuring and reporting actual wait times experienced by patients of doctors or other healthcare service providers. In accordance with the preferred embodiment, a patient launches the application on their mobile device and views a dashboard of their upcoming appointment, the scheduled appointment time, and the actual current wait time. A provider launches the application on the mobile device, and views a dashboard of upcoming patients, their current location within the office, and how long they have been waiting at their location. The provider dashboard is color-coded to indicate if a patient is alone or with a certain provider. The application, when opened in the office, will range nearby Bluetooth Low Energy (BLE) beacons, and determine the actual location of the patient or provider within the office. Utilizing the location of patients and providers, as well as open exam rooms and other components, the mobile application feeds this information into an algorithm that predicts the actual wait time for future patients.

Utilizing the location of patients, front desk staff will be notified when a patient enters the waiting room and when patients have waited an extensive period of time in an exam room. After the application determines a patient has entered the office, it will automatically check the patient in and push this change to the provider's electronic medical record ("EMR") system. The application will determine when a patient has left the office and automatically check out any patients within the EMR system if they haven't already been manually checked out. The application will also send a satisfaction survey to the patient once the patient is out of range of the office for a certain period of time. Patients will be notified of significant changes to their expected wait time and can utilize an in-app chat function to talk directly with providers and staff. Providers and office staff have the ability to notify future providers individually or in groups, when a patient is ready to be seen by a future provider (should they need to be seen by multiple providers in one visit). The application tracks the response time to messages and can report on the location data collected throughout the day to give transparency into doctor office efficiencies (based on check-in time, time to respond to messages, etc.).

The application is also capable of manually inputting a patient's location, should a patient not have a mobile phone or not wish to download the application. Patients will have the ability to cancel upcoming appointments and the algorithm will adjust wait times accordingly and as upcoming patients if they would like to be seen sooner. Patients will also have the ability to confirm insurance, demographic information, and pay for their appointment within the application.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The various embodiments are illustrated by way of example, and not by way of limitation, in the figures of the accompanying drawings. Having thus described the invention in general terms, reference will now be made to the accompanying drawings, which are not necessarily drawn to scale, and wherein:

FIG. 8 shows the location settings for the BLE beacons associated with the present invention.

FIG. 9 depicts an exemplary list of data collected by the present invention.

FIGS. 12A-B show the opening screen associated with the present invention and the set-up screen associated with the present invention.

DETAILED DESCRIPTION OF THE DRAWINGS

Figure 1:
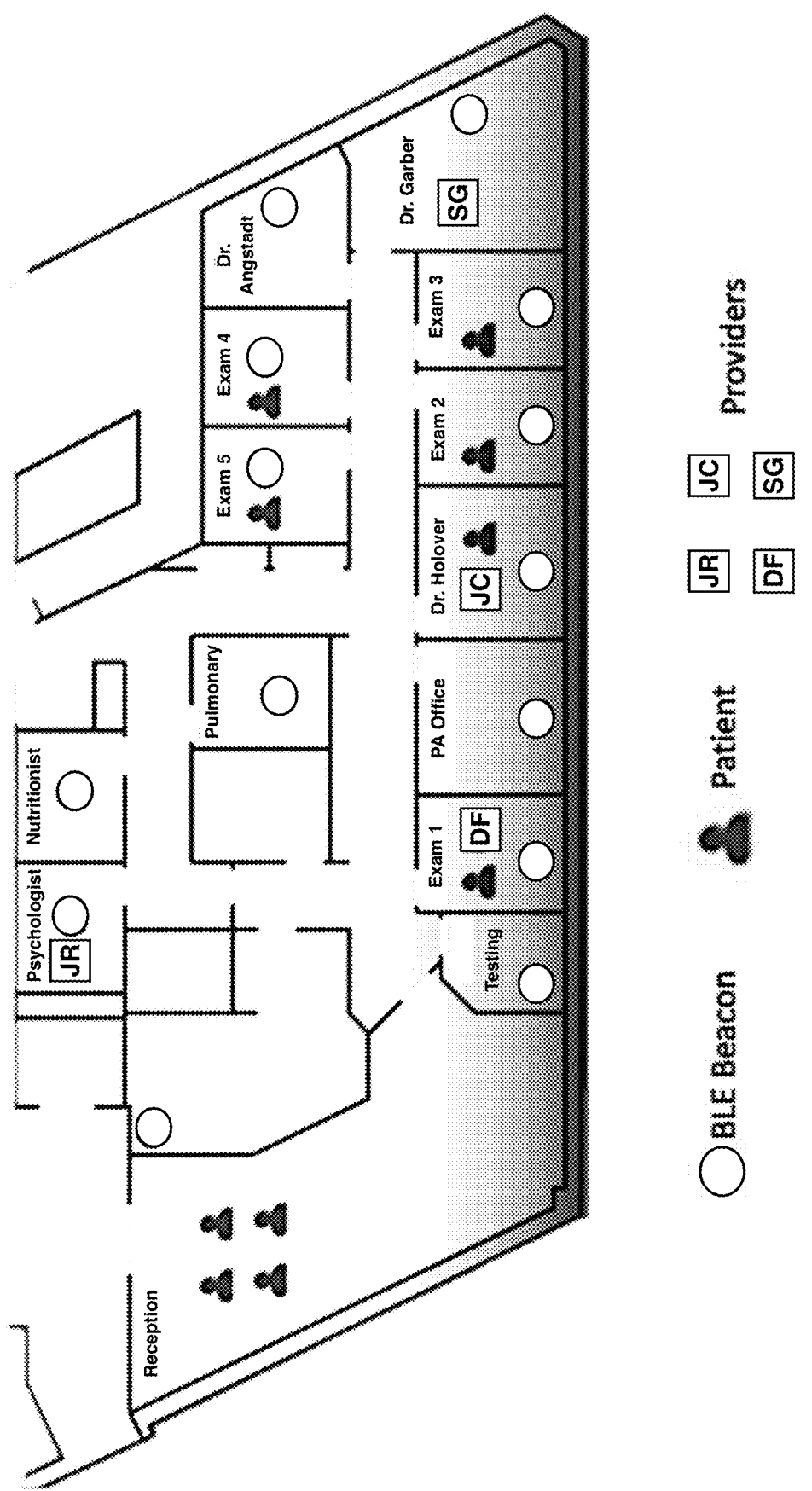
FIG. 1 shows placement of BLE beacons in an office space for tracking and analyzing wait times.

FIG. 1 shows placement of BLE beacons in an office space for tracking and analyzing wait times. In accordance with the preferred embodiment of the present invention, each patient's phone or other mobile device and each provider's phone or other mobile device will sense the nearest beacon to determine where the person is within the office. The application will use this information to create a dashboard of the current office outlook for staff, accessible via a user interface. The application also uses this information to notify relevant personnel when they need to take a certain action.

In accordance with the preferred embodiment of the present invention, the beacons provide an ability to identify where patients and providers are within the office utilizing Bluetooth connection. A mobile "Bluetooth Ranging" application module (implemented as a native iOS and Android code) can monitor BLE beacon signal strength and send to location services. A location microservice with the ability to receive mobile ranging location data from the application generates (and saves) historical location update events for each user (patient, provider, staff, or other user) "session" and publishes these events to be used by the scheduling microservice. A refactor or upgrade of location service (implemented as web service lambda functions) to simplify a location resolution algorithm and allow the mobile application to optimize and minimize both the on-device processing and transmitted data size requirements for the mobile Bluetooth ranging code. The present invention is therefore able to ensure tracking is accurate and agile.

Figure 2:
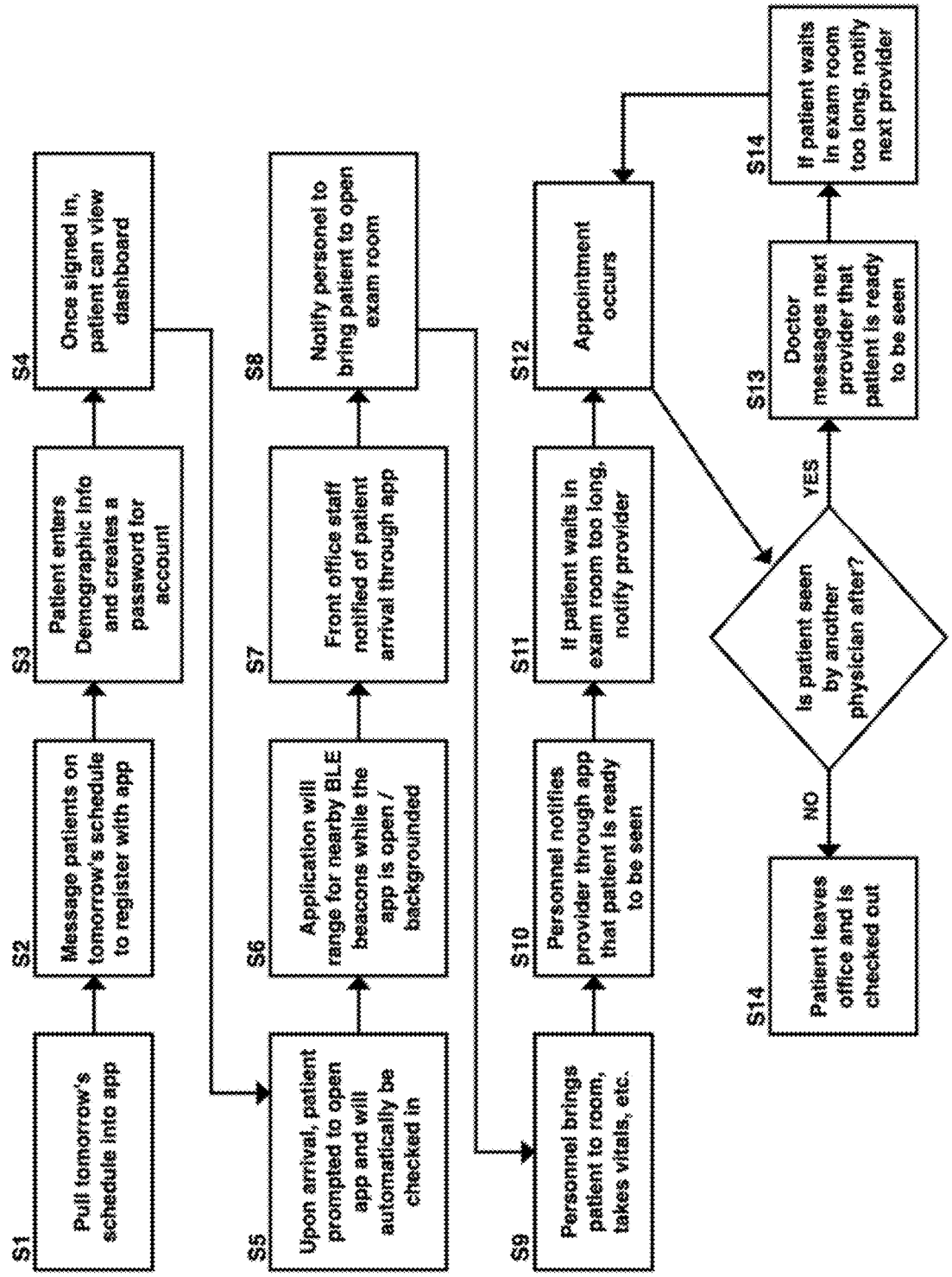
FIG. 2 shows the process flow of the application with regard to patients.

FIG. 2 shows the process flow of the application with regard to patients. In accordance with the preferred embodiment of the present invention, the application pulls each doctor's schedule for the following day into the application. Then, the application notifies, via push notification, email, text, or other methods, all patients on the schedule for tomorrow with a registration link associated with the application. The patients are then prompted to enter demographic information and create a password for their account if they have not done so already. Once the patient is signed in, they can view a dashboard of their upcoming appointment with information regarding the doctor or care provider, appointment time, and current wait time via a user interface. Upon arrival, the patient's phone or other mobile device will sense the practice's BLE beacons and prompt them to open the application and they will automatically be checked in for their appointment. The application will range nearby BLE beacons while the app is open or backgrounded. The front staff is then notified as to when a patient has checked in to confirm demographic information, insurance information, and other requested patient information or patient data.

When an exam room is available for the patient, the relevant personnel is notified to bring the patient to the exam room. Personnel brings the patient to the exam room, spends some time with them (taking vitals etc.) then notifies the doctor or other care provider through the application that the patient is ready to be seen. Upon the patient waiting an amount of time predetermined by the office (for example, and not by way of limitation, after the patient has waited ten minutes) in the exam room, the care provider is notified. Upon the patient waiting an amount of time predetermined by the office (for example, and not by way of limitation, after the patient has waited ten minutes) in the exam room, the care provider is notified. The doctor or other care provider then conducts the appointment with the patient. If another care provider is needed, the previous care provider can message the next care provider through the application to indicate that the patient is ready to be seen. This is especially helpful for physician's assistants and nurses to alert physicians after an initial screening is conducted. Once the appointment has concluded, the patient exits the office and is either manually checked out at the front desk or they may check out using the application as it is connected to the office's EMR system.

Figure 3:
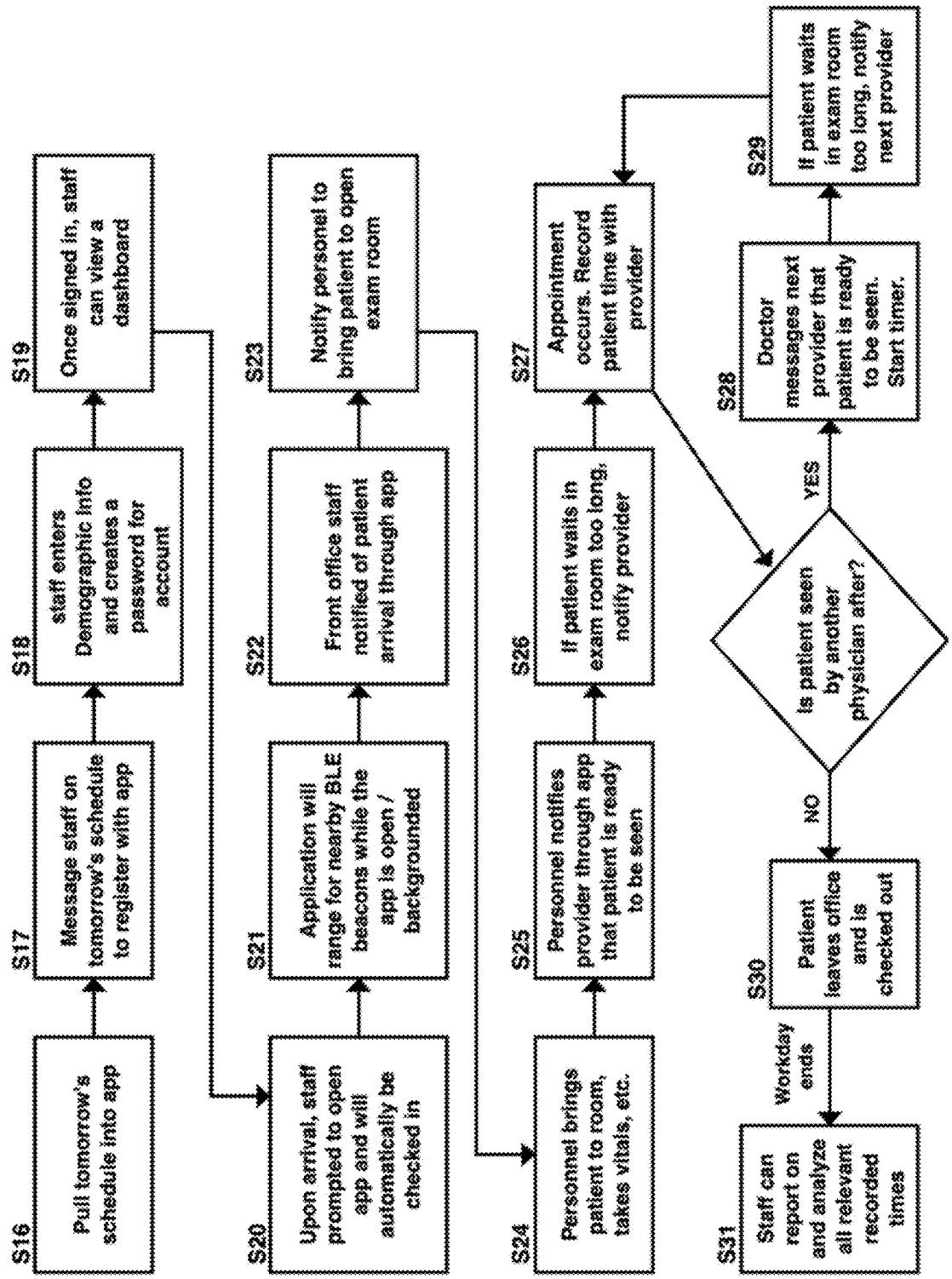
FIG. 3 shows the process flow for the application with regard to staff.

FIG. 3 shows the process flow for the application with regard to staff. In accordance with the preferred embodiment of the present invention, the application pulls each doctor's schedule for the following day from the doctor's EMR system. The application then notifies, via push notification, email, text, or other methods, all staff on the schedule for the following day with a registration link. The link directs the staff to enter demographic information and create a password for the account. Once the staff is signed in, they can view a dashboard of their upcoming day including information regarding patients, appointment times, current patient locations within the office (or beyond, if enabled by the patient), and how long a patient has been waiting via a user interface. Upon arrival, the staff member's phone or other mobile device will sense the practice's BLE beacons and prompt them to open the application. The application will record which staff are in the office.

The application will range for nearby BLE beacons while the application is open or backgrounded. The front office staff is notified when a patient has checked in to confirm demographic information, insurance information, and any other requested patient information or patient data. When an exam room becomes available for a patient, the relevant staff is notified to bring the patient to the exam room. Personnel brings the patient to the exam room, spends some time with them (taking vitals etc.) then notifies the doctor or other care provider through the application that the patient is ready to be seen. Upon the patient waiting an amount of time predetermined by the office (for example and not by way of limitation, after the patient has waited ten minutes) in the exam room, the care provider is notified. The appointment is then conducted, and a time that the patient spends with the care provider is recorded. The care provider then messages or notifies the next care provider through the application that the patient is ready to be seen. Patient wait time between care providers is then recorded. Upon the patient waiting an amount of time predetermined by the office (for example and not by way of limitation, after the patient has waited ten minutes) in the exam room, the care provider is notified. Once the appointment has concluded, the patient exits the office and is either manually checked out at the front desk or checks out using the application as it is connected to the office's EMR system. The application consists of a robust reporting system capable of analyzing all relevant recorded data including patient wait times, appointment times, patient cancellations, patient arrival times, and other important data.

Figure 4:
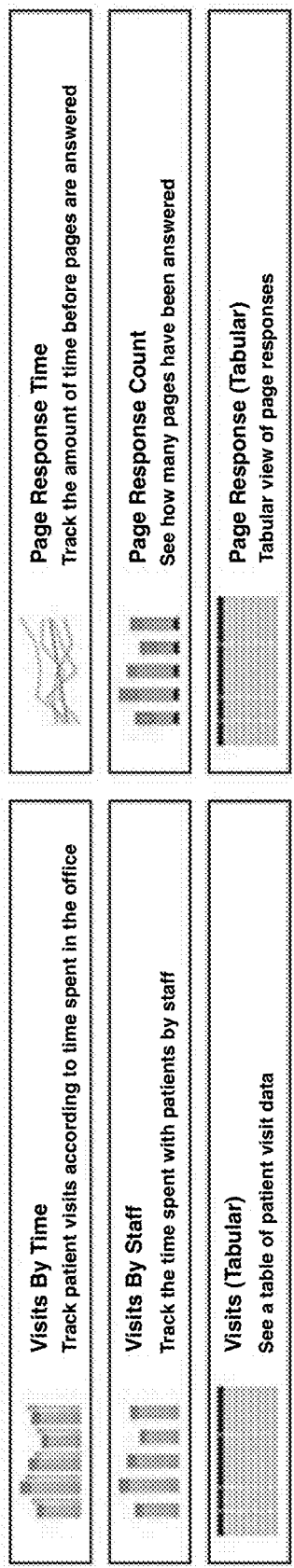
FIG. 4 shows reporting capabilities and different reports that can be generated.

FIG. 4 shows reporting capabilities and different reports that can be generated. In accordance with the preferred embodiment, the report system within the administration portal shows the reporting capabilities and different reports that can be generated. For example, and not by way of limitation, these include visits by time, visits by staff, visits in a table, message response times, message count, message count in a table, among other reports.

Figure 5:
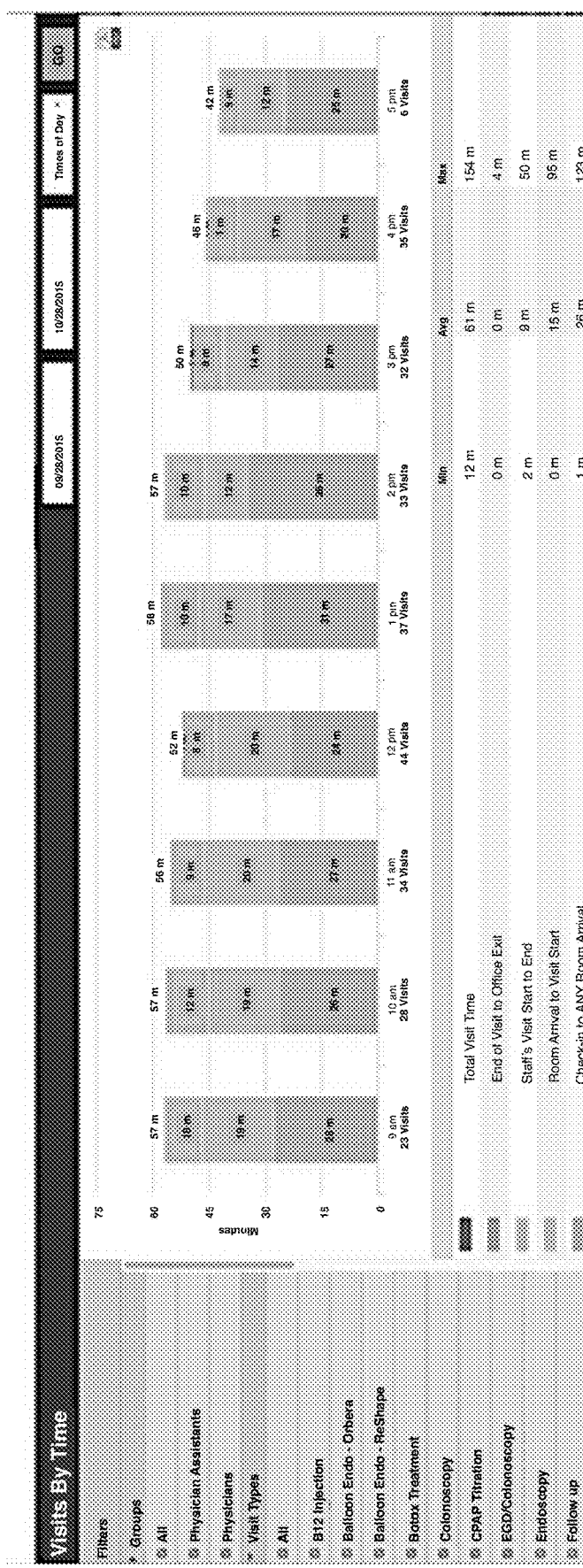
FIG. 5 shows an example of reporting capabilities, specifically visits by time.

FIG. 5 shows an example of reporting capabilities, specifically visits by time. In accordance with the preferred embodiment of the present invention, the application reporting capabilities include reports regarding visits by time. For each hour of the day, appointments are grouped into a column, and the average wait time at each step of the appointment is calculated and shown in a different color. There is a key at the bottom of the page to describe the corresponding colors. The key also includes a table with the minimum, maximum, and average time for each step based on the day the data is recorded. In some embodiments of the present invention, wait time data is analyzed via a machine-learning algorithm and wait time predictions are generated based on the patient, the reason for visit, the time of day, the date, and other factors that may impact wait time. This enables the present invention to provide accurate predictions for wait times for scheduled patients and to increase efficiency within the office.

Figure 6:
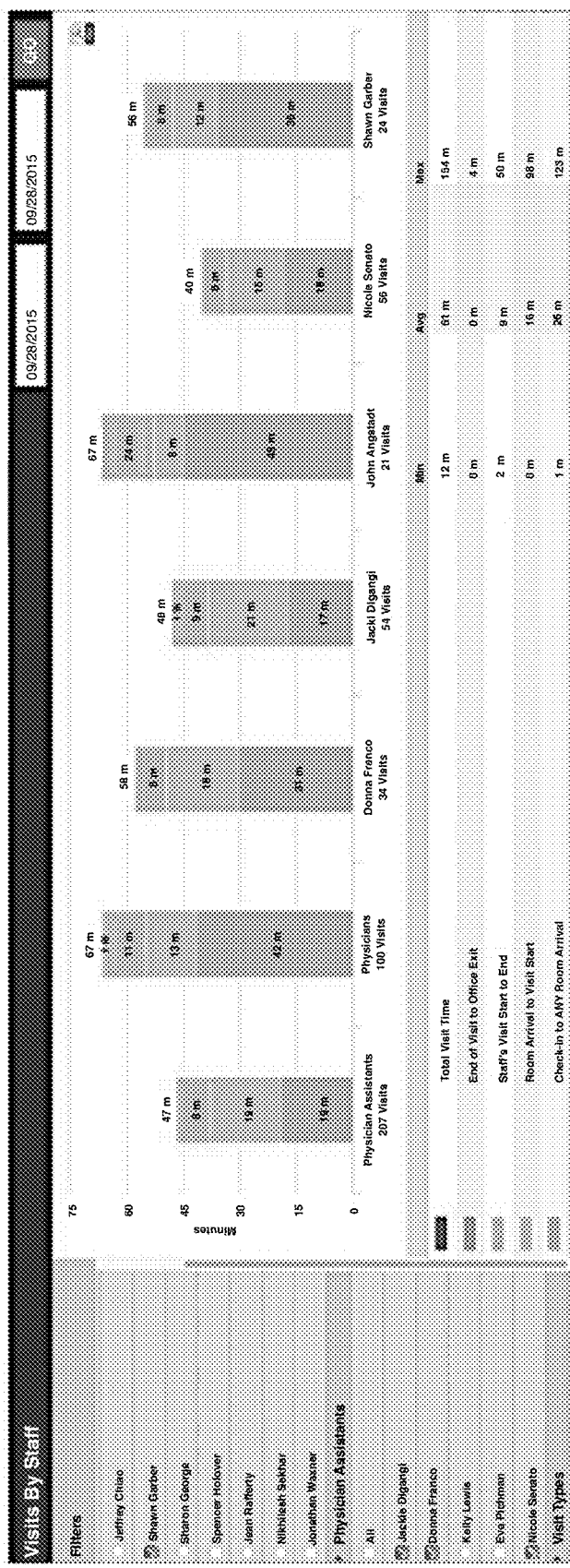
FIG. 6 shows an example of reporting capabilities, specifically visits by staff.

FIG. 6 shows an example of reporting capabilities, specifically visits by staff. In accordance with the preferred embodiment of the present invention, the application reporting capabilities include reports regarding visits by staff. For each staff member or staff group, appointments are grouped into a column, and the average wait time at each step of the appointment is calculated and shown via a different color. There is a key on the bottom of the page to describe the corresponding colors. The key also includes a table with the minimum, maximum, and average time for each step based on the day the data is recorded.

Figure 7:
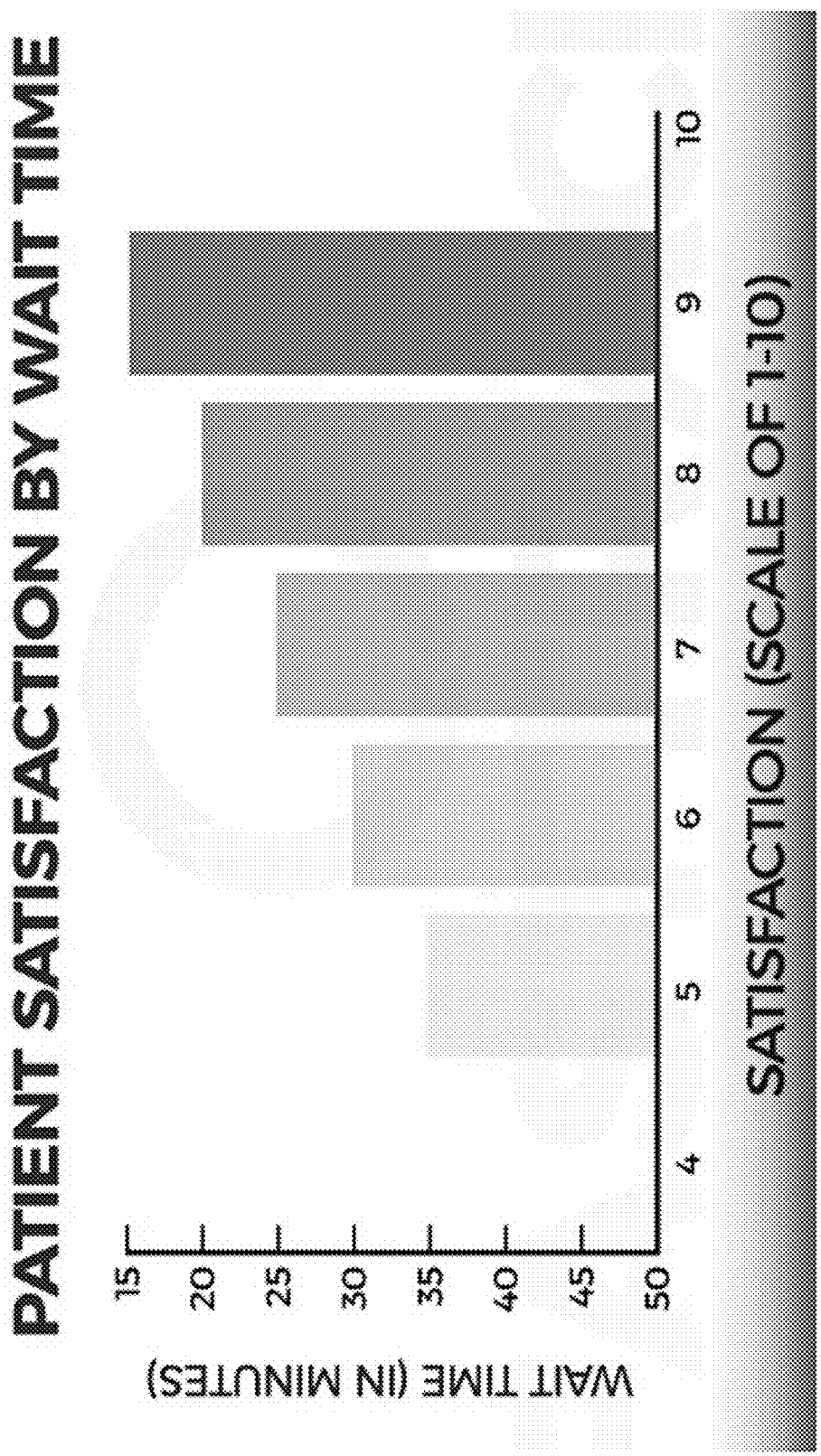
FIG. 7 shows an example of reporting capabilities, specifically patient satisfaction by wait time.

FIG. 7 shows an example of reporting capabilities, specifically patient satisfaction by wait time. In accordance with the preferred embodiment of the present invention, patient satisfaction scores are provided via a graph or plurality of graphs based on the wait times the patients experienced. As patient wait time decreases, patient satisfaction increases.

FIG. 8 shows the location settings for the BLE beacons associated with the present invention. In accordance with the preferred embodiment of the present invention, a plurality of settings are available for a provider or staff member to view or edit under the location settings. For example, and not by way of limitation, a minimum number of seconds in the room can be set, along with a minimum number of consecutive pings, a weak signal floor, a maximum signal ceiling, a number of minutes for ranging timeout, a number of minutes after checkout to stop tracking, and a number of minutes after no ranging to checkout can be set based on staff or provider preferences. Information regarding each of these settings is provided to the user for further clarification.

FIG. 9 depicts an exemplary table of data collected by the present invention. In accordance with the preferred embodiment of the present invention, a user can save a plurality of locations in which the present invention is deployed. Each row depicted in FIG. 9 (not including the first row of titles) represents a BLE beacon associated with the present invention. The first column from the left, titled "PracticeName," provides the name of the practice using the present invention. For example, and not by way of limitation. The second column from the left, titled "OfficeName," provides a list of specific office locations associated with the practice. For example, and not by way of limitation, the practice "New York Bariatric Group" has at least two offices, one located in Roslyn and the other located in Westchester. The third column from the left, titled "RoomName," provides a list of specific rooms associated with each office. For example, and not by way of limitation, The Roslyn office has at least three rooms saved within the system, namely "Exam 1," "Exam 2," and "reception." The fourth column from the left, titled "avg_median_" provides the average median for each room. The fifth column, titled "num_pings_," provides the number of pings received via the BLE beacons within each room. The last column, titled "last_ping," provides the date and time of the last ping received from each BLE beacon.

Figure 10A:
FIGS. 10A-O show exemplary views of the present invention as accessed via a physician or care provider.

FIGS. 10A-I show exemplary views of the present invention as accessed via a physician or care provider. In accordance with the preferred embodiment of the present invention, the care provider dashboard provides a table or map of the location and status of all patients for the day. FIG. 10A depicts an example of the map presented to a care provider. For example, and not by way of limitation, the map may present a table including room, room status, provider/staff, patient, patient status, wait time, time in office, and appointment time information. To the left of the table, a list of additional screen options can be found, including options to view a dashboard, a list of patients and relevant patient information, a list of staff and relevant staff information, a list of groups and relevant group information, a list of reports, a settings option to customize the present invention, and a support option for troubleshooting. The dashboard may be color coded for viewing convenience.

Figure 10B:
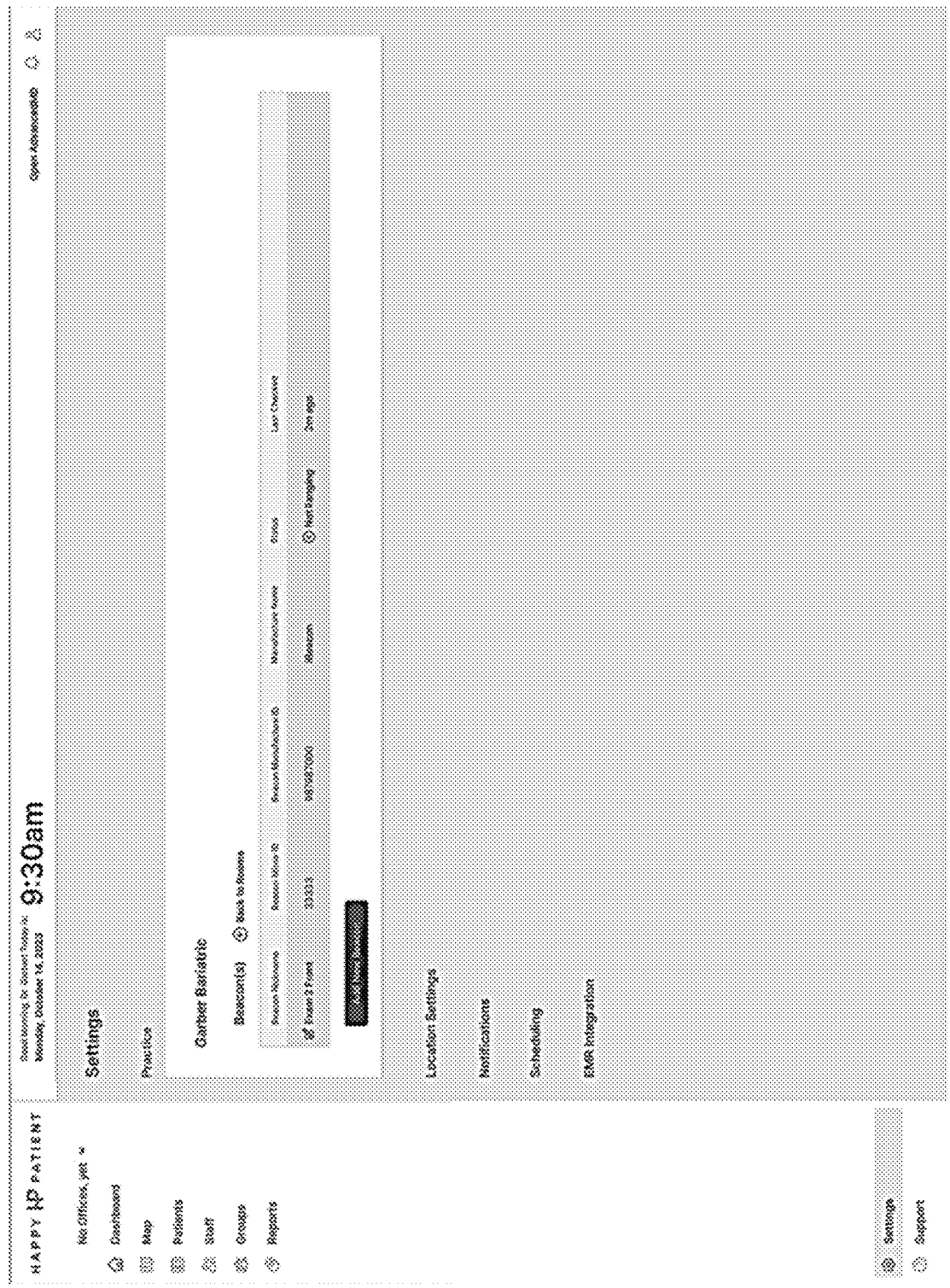

FIG. 10B depicts the settings associated with the present invention. In accordance with the preferred embodiment of the present invention, a user may edit, add, and remove BLE beacons from their system via the settings webpage. A user can also access BLE beacon information including BLE beacon nickname, beacon Minor ID, beacon manufacturer ID, manufacturer name, beacon status, and the time at which the beacon was last checked. A user can also access location settings, notifications settings, scheduling settings, and EMR integration settings.

Figure 10C:

FIG. 10C shows an example of how a user may create a new saved location associated with the present invention. In accordance with the preferred embodiment, a user simply inputs a name, the street address, city, state, postal or zip code, and phone number associated with the new location.

Figure 10D:
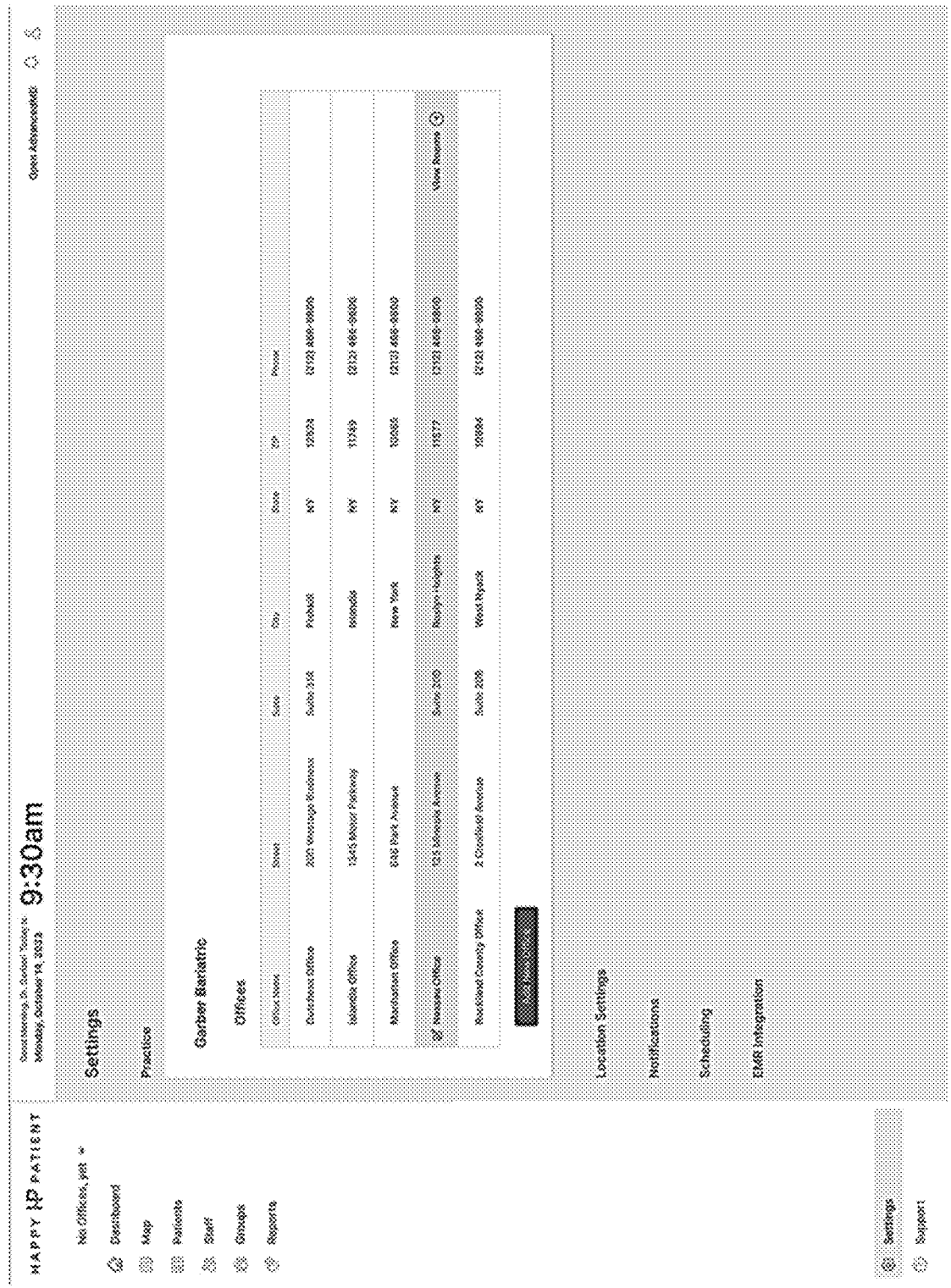

FIG. 10D depicts an example of the practice settings view of the present invention. In accordance with the preferred embodiment of the present invention, a user may edit, add, and remove a plurality of saved locations or "offices" associated with the present invention.

Figure 10E:

FIG. 10E depicts an example of the practice settings of the present invention. In accordance with the preferred embodiment of the present invention, a user may view a plurality of rooms or spaces associated with each saved location or "office." A user may also view the number of beacons located in each room or space and the status of each beacon in each room or space.

Figure 10F:
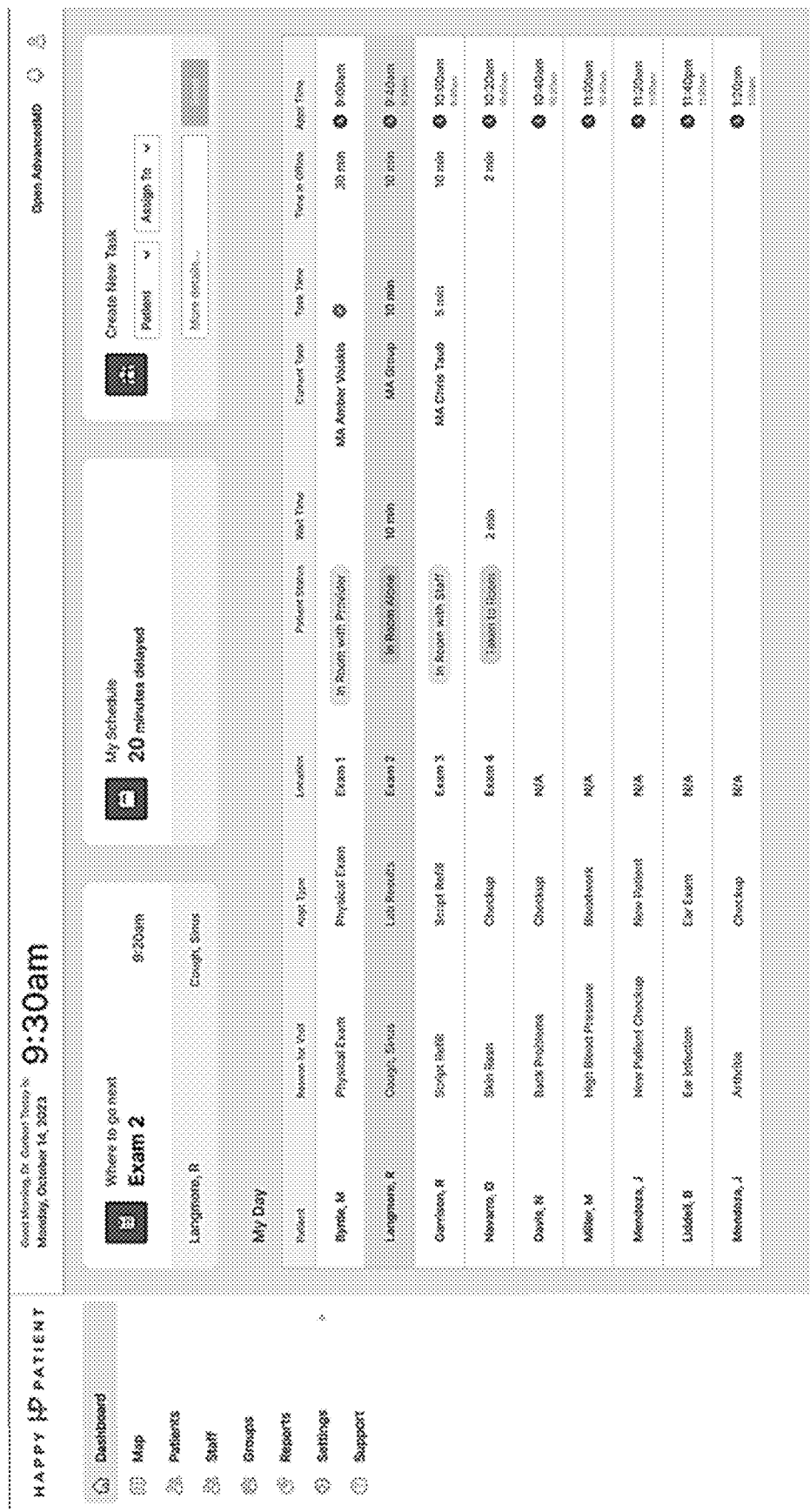

FIG. 10F depicts an example of the dashboard screen as viewed by a care provider. In accordance with the preferred embodiment of the present invention, the dashboard provides an overview of relevant information including upcoming appointment information, an overview of the day including scheduled patients, reason for patient visits, appointment types, locations, patient status, patient wait times, current tasks, task time till completion, time each patient has spent in the office, and appointment time. The dashboard also provides the opportunity to create and assign new tasks to other staff members, for example "blood draw," "EKG," and other tasks. While a plurality of tasks may be assigned to staff members, other tasks may be completed automatically by the system, which may be triggered based on the detected location of a care provider, staff member, or patient. The location of each task is automatically assigned based on patient location. For example, and not by way of limitation, if the task "blood draw" is assigned to a patient waiting in Exam Room 2, the provider or staff member assigned to the task will be notified to go to Exam Room 2 to complete the task. The "assign to" drop down list shows all available providers and staff members and groups to whom the task may be assigned. The dashboard also provides the ability to send free form messages with tasks and integrate tasks with a scheduling service. Tasks may be stacked to occur at the same time, or across multiple times.

Furthermore, the present invention has the ability to create data views for reporting to summarize stored microservice events to generate and save dimensions (i.e., practice, office, provider, appointment type, day, time, and other factors) and measures (i.e., appointment duration, patient wait time, and other measures) to be consumed by administration reports. The reporting and analysis framework generates web-ready analytics and reporting and is embedded and implemented for access to reporting views within the administration portal or mobile application.

Figure 10G:
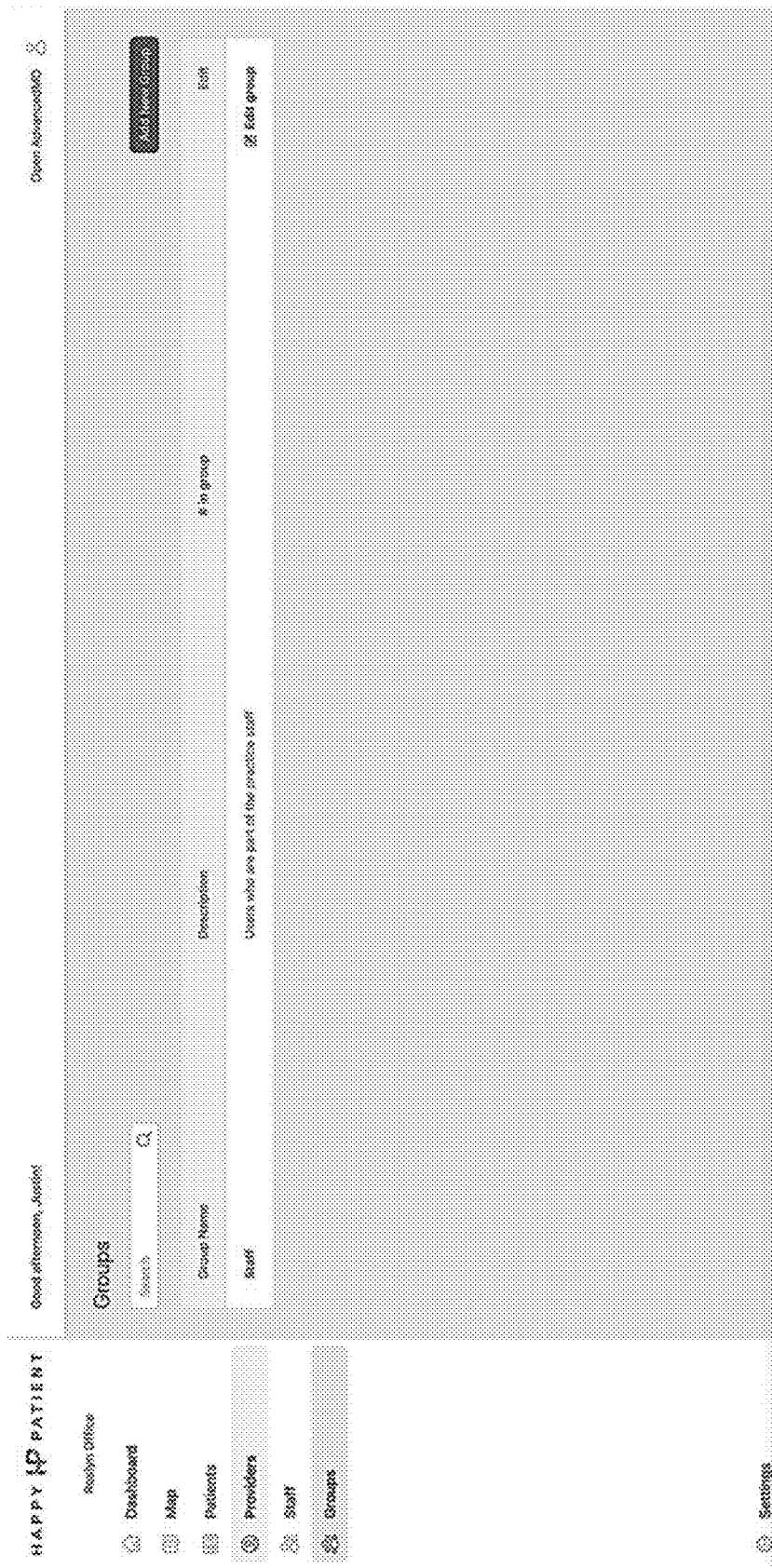

FIG. 10G shows an exemplary view of the Groups tab of the present invention. In accordance with the preferred embodiment, a care provider can create categorized groups of individuals using the present invention in association with the care provider. For example, and not by way of limitation, a care provider may create a "staff" group as shown in FIG. 10G. The provider can input a description of the group and add users to the group in order to streamline messaging, tasks, and other aspects of the present invention.

Figure 10H:
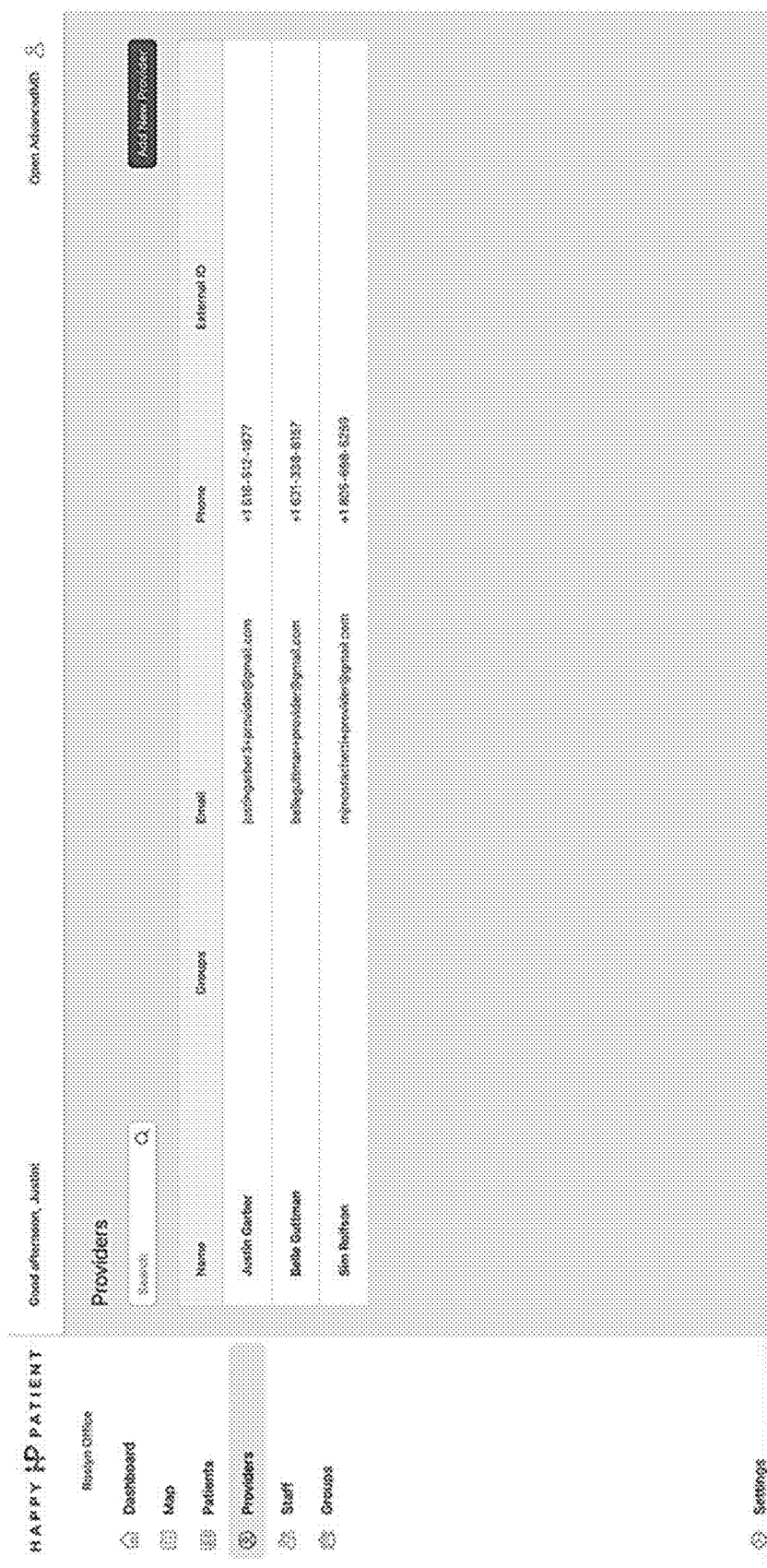

FIG. 10H shows an exemplary view of the Providers tab of the present invention. In accordance with the preferred embodiment of the present invention, A plurality of care providers can be entered into the system of the present invention and accessed via the "Providers" tab. If a provider is assigned to a group, their assigned group will populate on the screen along with their email, phone number, and optionally, their external identification ("ID").

Figure 10I:
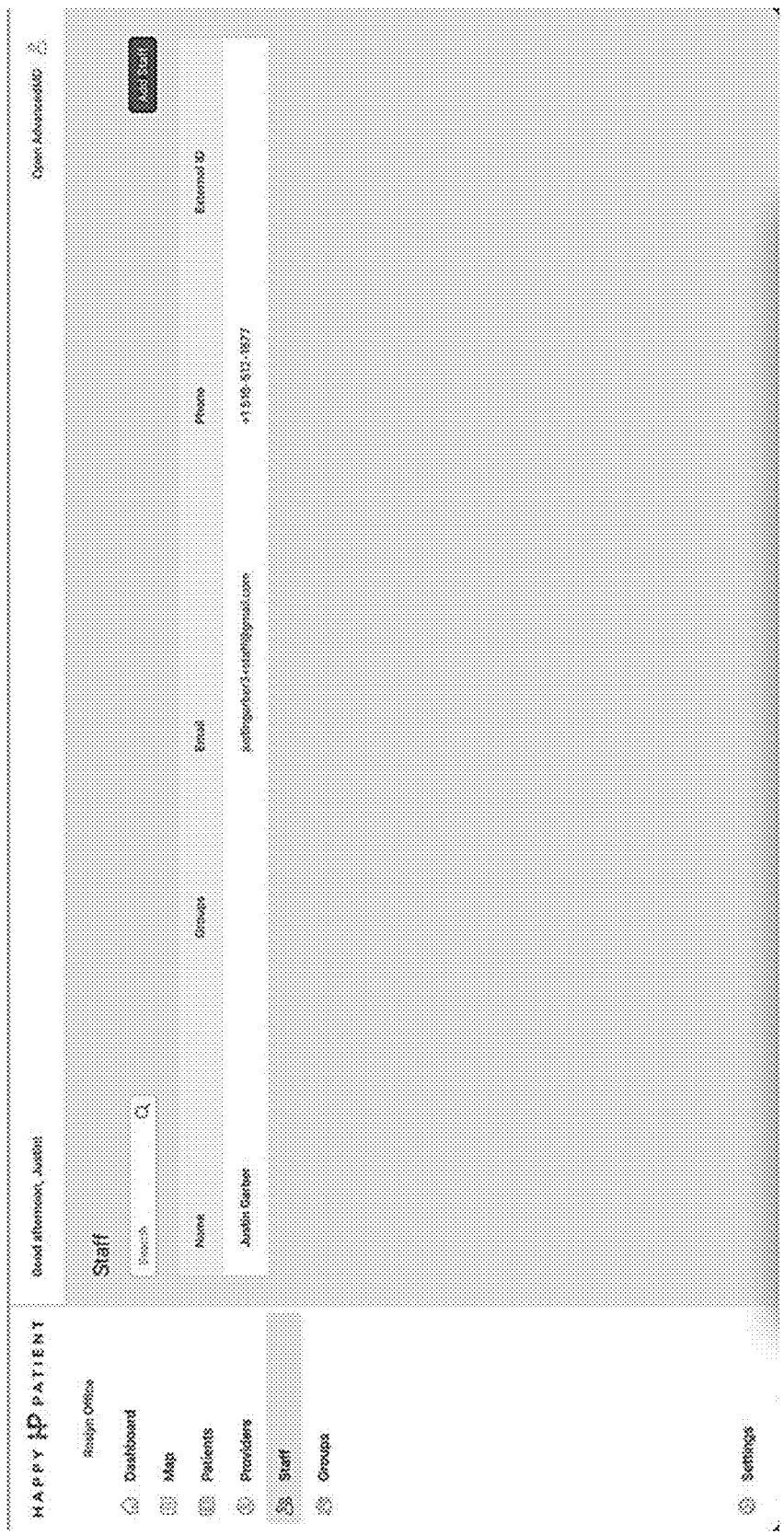

FIG. 10I shows an exemplary view of the Staff tab of the present invention. In accordance with the preferred embodiment of the present invention, a plurality of staff members can be entered into the system of the present invention and accessed via the "Staff" tab. If a staff member is assigned to a group, their assigned group will populate on the screen along with their email, phone number, and optionally, their external ID.

Figure 10J:
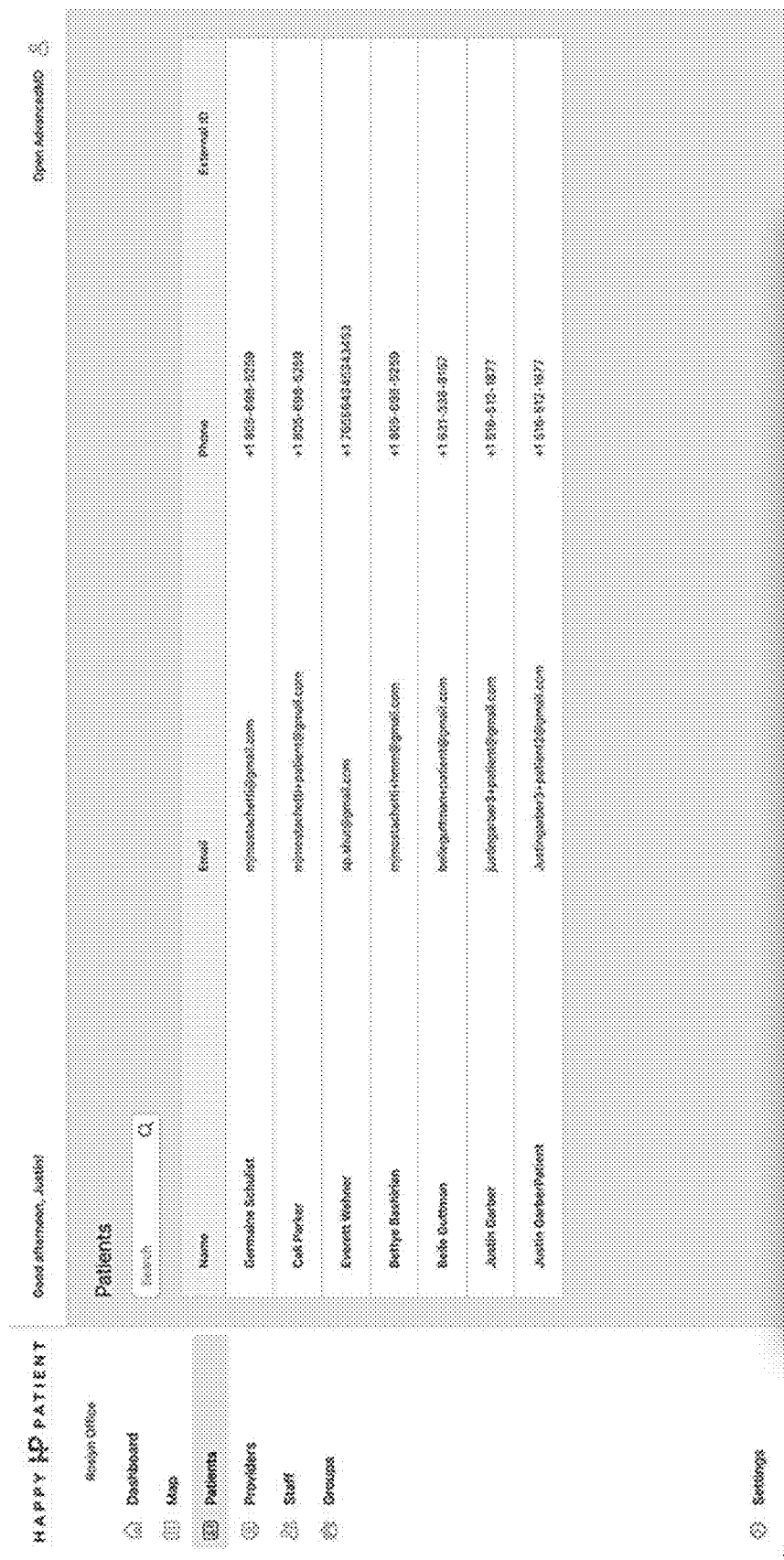

FIG. 10J shows an exemplary view of the Patients tab of the present invention. In accordance with the preferred embodiment of the present invention, a plurality of patients can be entered into the system of the present invention, and each patient's name, email, phone number, and external ID can be viewed under the Patients tab.

Figure 10K:
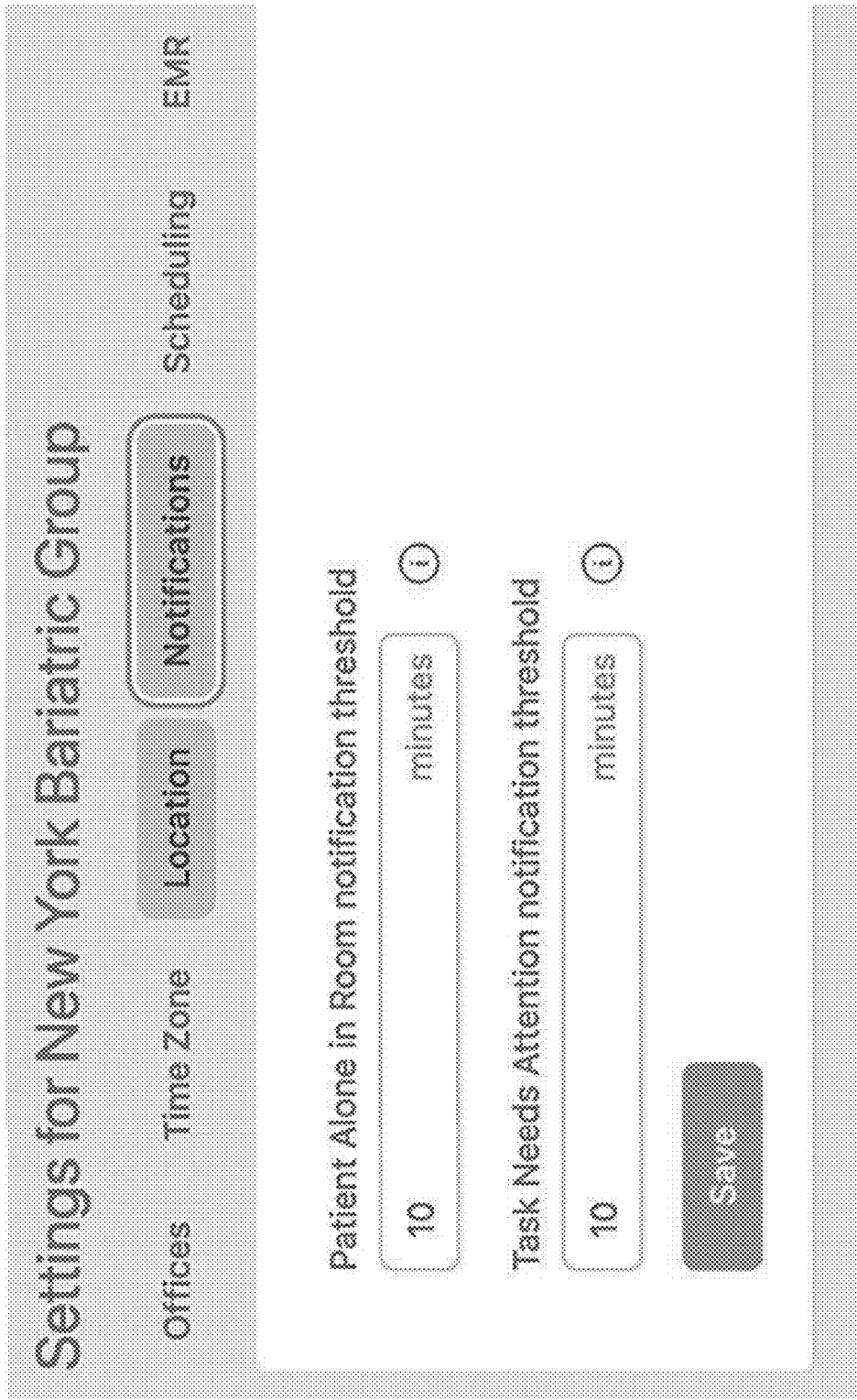

FIG. 10K shows an exemplary view of the notifications settings of the present invention. In accordance with the preferred embodiment of the present invention, at least one notification can be scheduled to send after a patient has been waiting for a certain amount of time. For example, and not by way of limitation, a notification can be scheduled to send to the staff and care providers if the patient has been detected to be waiting along for 10 minutes.

FIG. 10L shows an exemplary view of the scheduling settings of the present invention. In accordance with the preferred embodiment of the present invention, a schedule for specific tasks can be set in order to track whether or not the daily schedule aligns with the real-time schedule, and to aid the system in making automatic scheduling adjustments when the real-time schedule does not align with the daily schedule. An amount of time for a task can be set, along with an amount of buffer time, an amount of time following the buffer, which is considered late, and a minimum patient notice before appointment schedule shift. For example, and not by way of limitation, a provider may decide that patient prep time will take 5 minutes, a buffer time of 15 minutes will be provided, at 5 minutes past the buffer time the provider is considered late, and a minimum time of 60 minutes is required to provide a notice to patients before a shift in the schedule occurs.

Figure 10M:
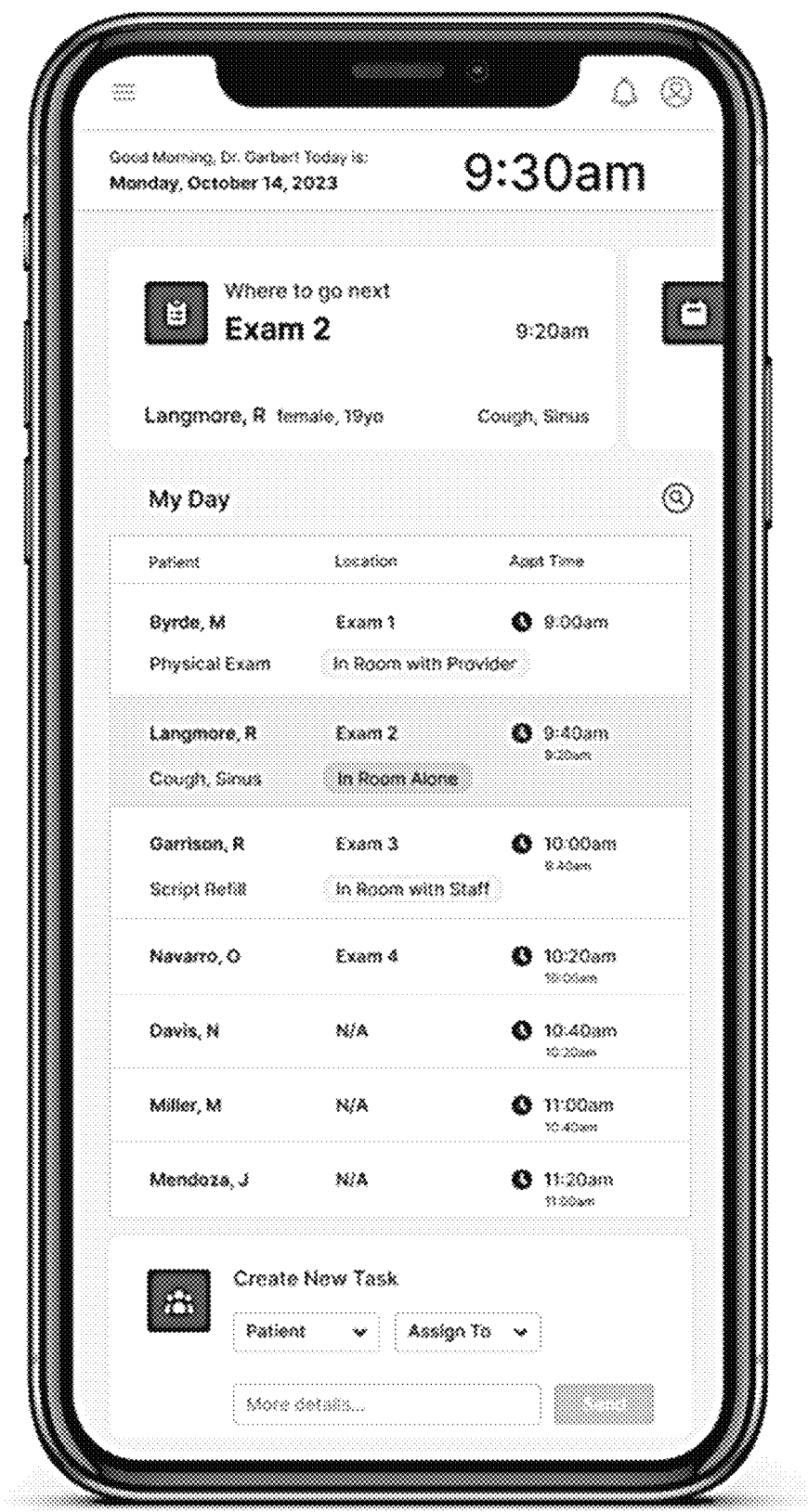
Figure 10N:
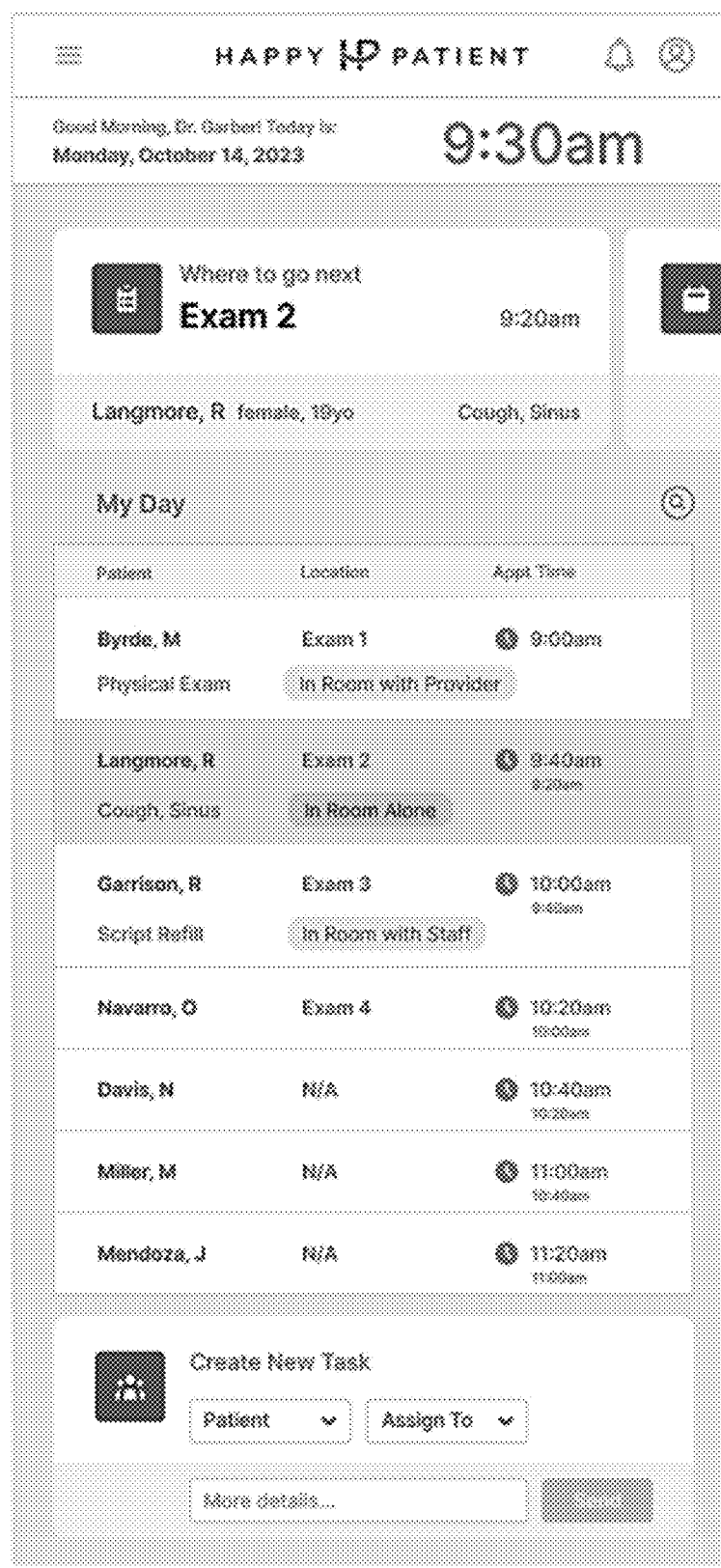
Figure 100:
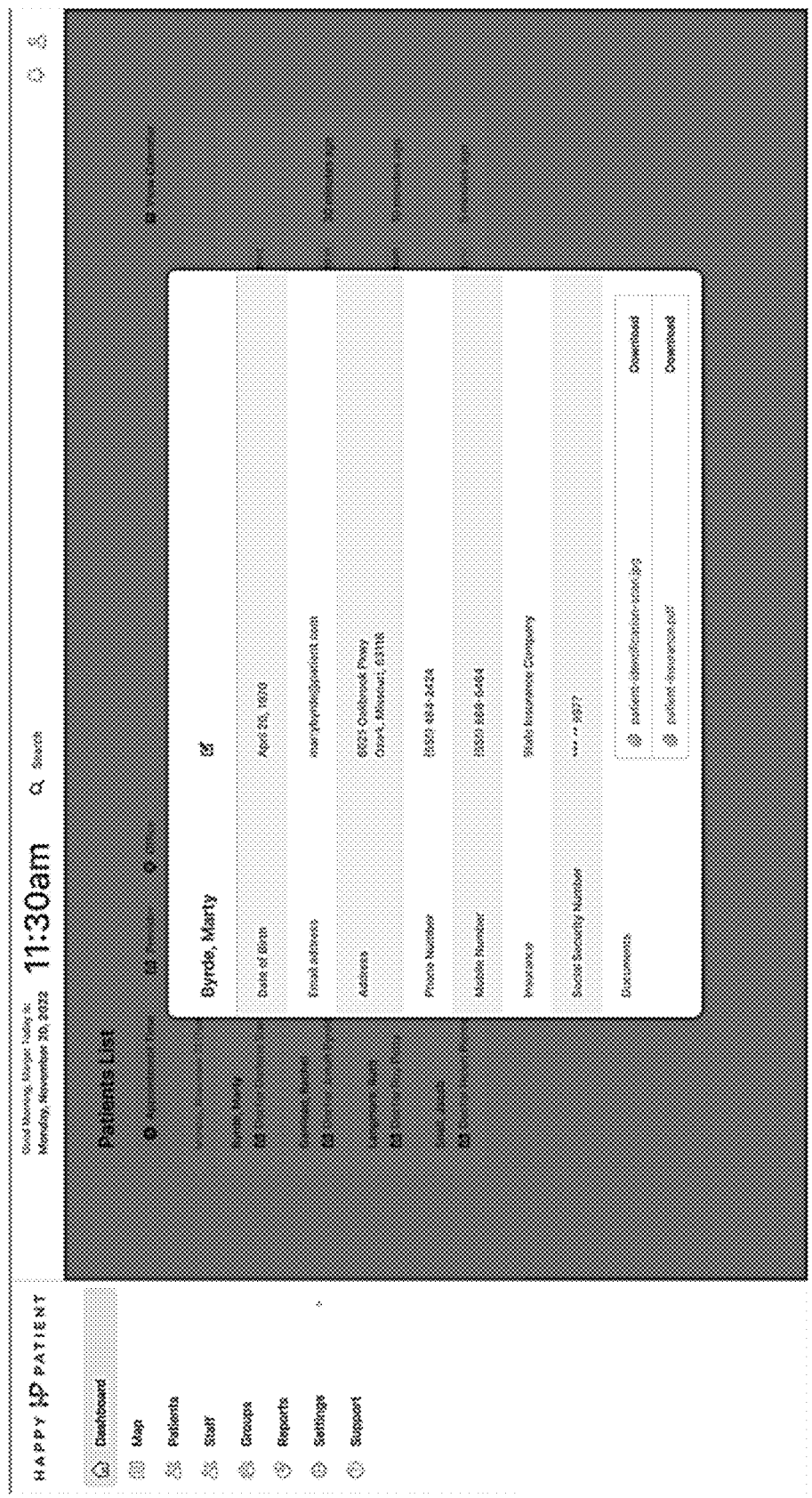

FIGS. 10M and 10N provide exemplary views of the dashboard as accessed by a care provider on a mobile device. In accordance with the preferred embodiment of the present invention, the dashboard as viewed on a mobile device provides most of the same information as viewed from a computer or monitor screen.

FIG. 10O depicts an exemplary view of patient demographic information as accessed by a care provider. In accordance with the preferred embodiment of the present invention, care providers and staff can access and edit patient demographic information including date of birth, email address, home address, home phone number, mobile phone number, insurance, social security number, and additional documents.

Figure 11A:
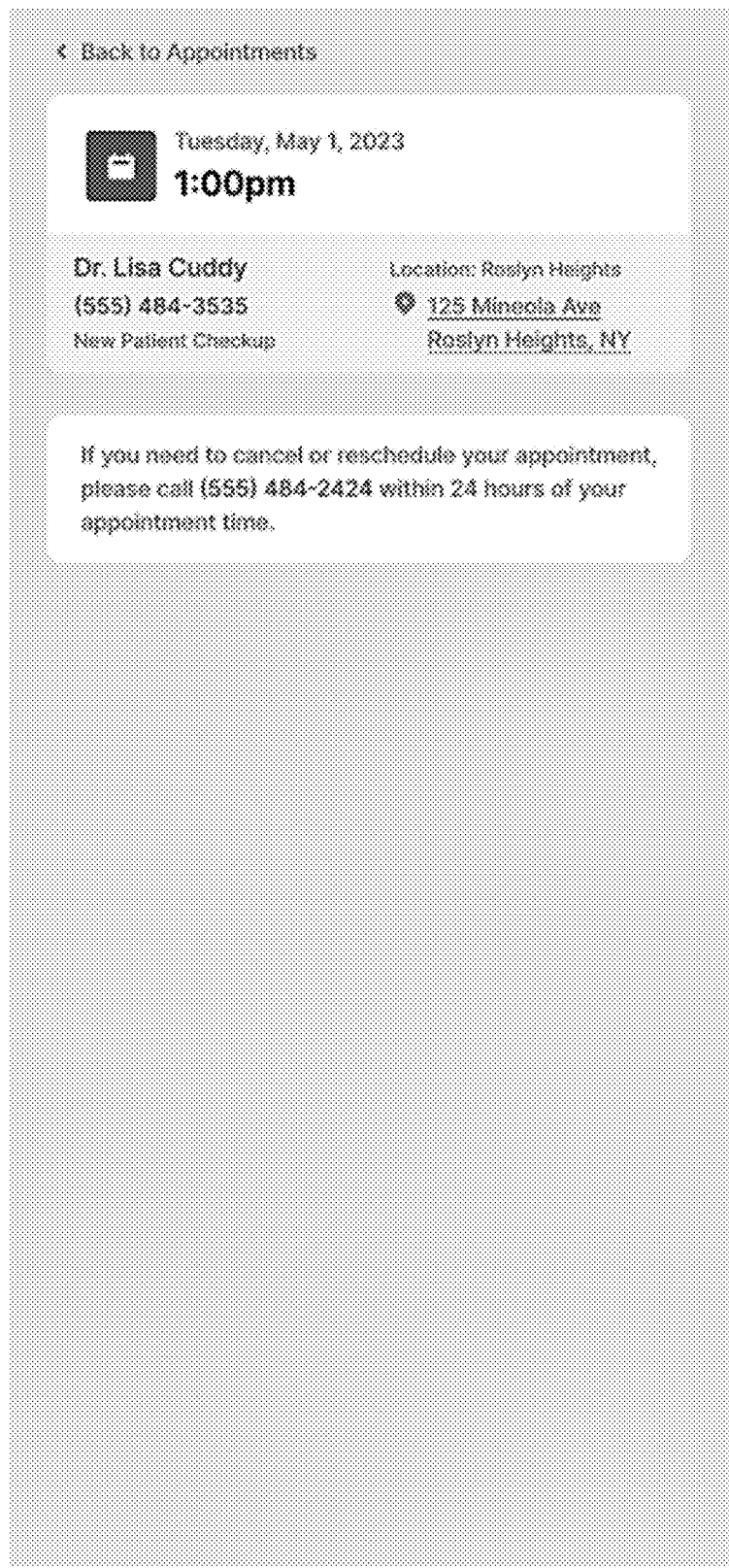
FIGS. 11A-E show exemplary views of the present invention as accessed via a customer or patient.

FIGS. 11A-D show exemplary views of the present invention as accessed via a customer or patient. FIG. 11A depicts an exemplary view of appointment details as accessed by a patient on a mobile device. In accordance with the preferred embodiment of the present invention, a patient may access appointment details including appointment date and time, location and address, care provider name and phone number, and care provider cancellation policy.

Figure 11B:
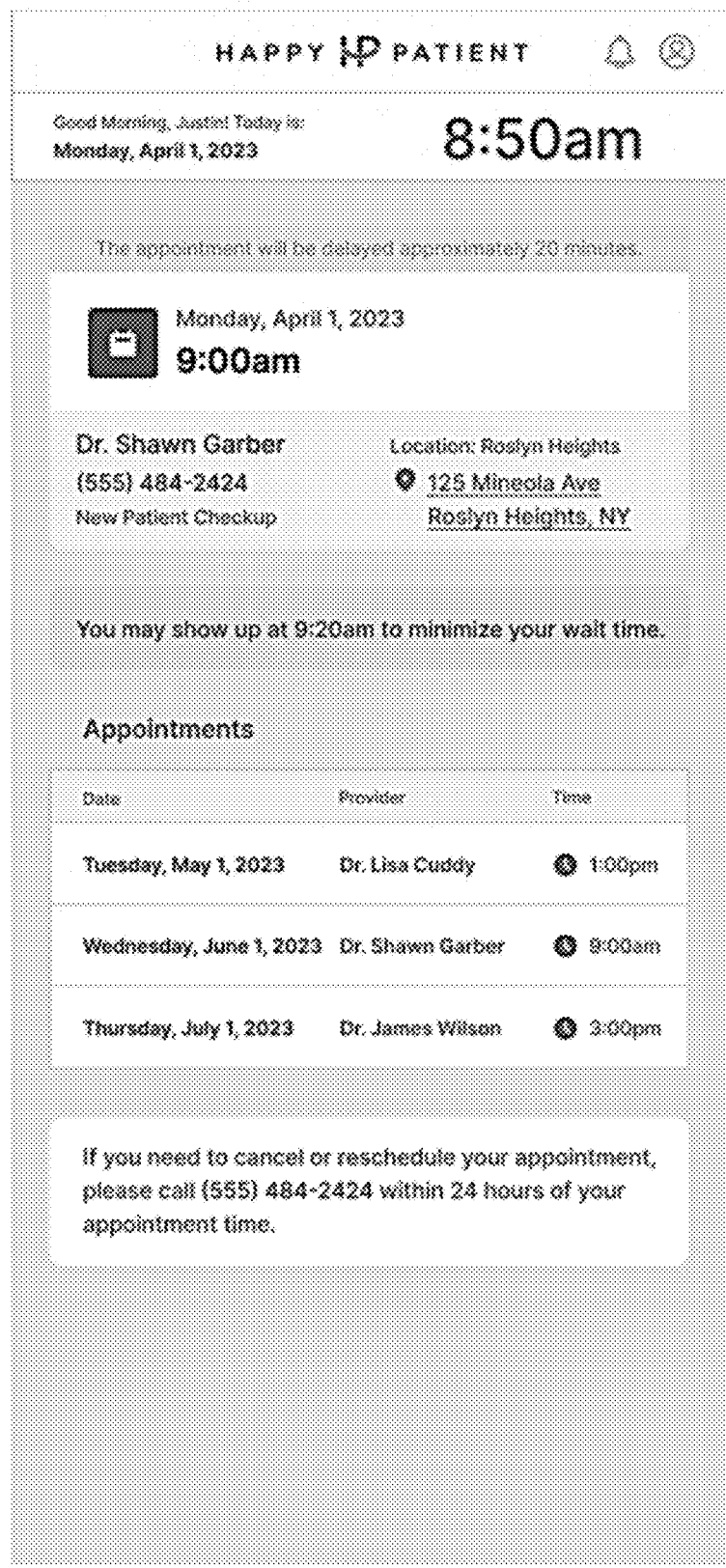

FIG. 11B depicts an example of the dashboard as accessed by a patient on a mobile device. In accordance with the preferred embodiment of the present invention, a patient's dashboard provides upcoming appointment information including appointment details for the next upcoming appointment, an amount of time for which the upcoming appointment might be delayed, a suggested time of arrival to avoid lengthily wait times at the appointment, and an overview of all future scheduled appointments.

Figure 11C:

FIG. 11C shows an exemplary view of provider details as accessed by a patient on a mobile device. In accordance with the preferred embodiment of the present invention, a patient may view information regarding the car provider with which the patient is schedule to meet.

Figure 11D:
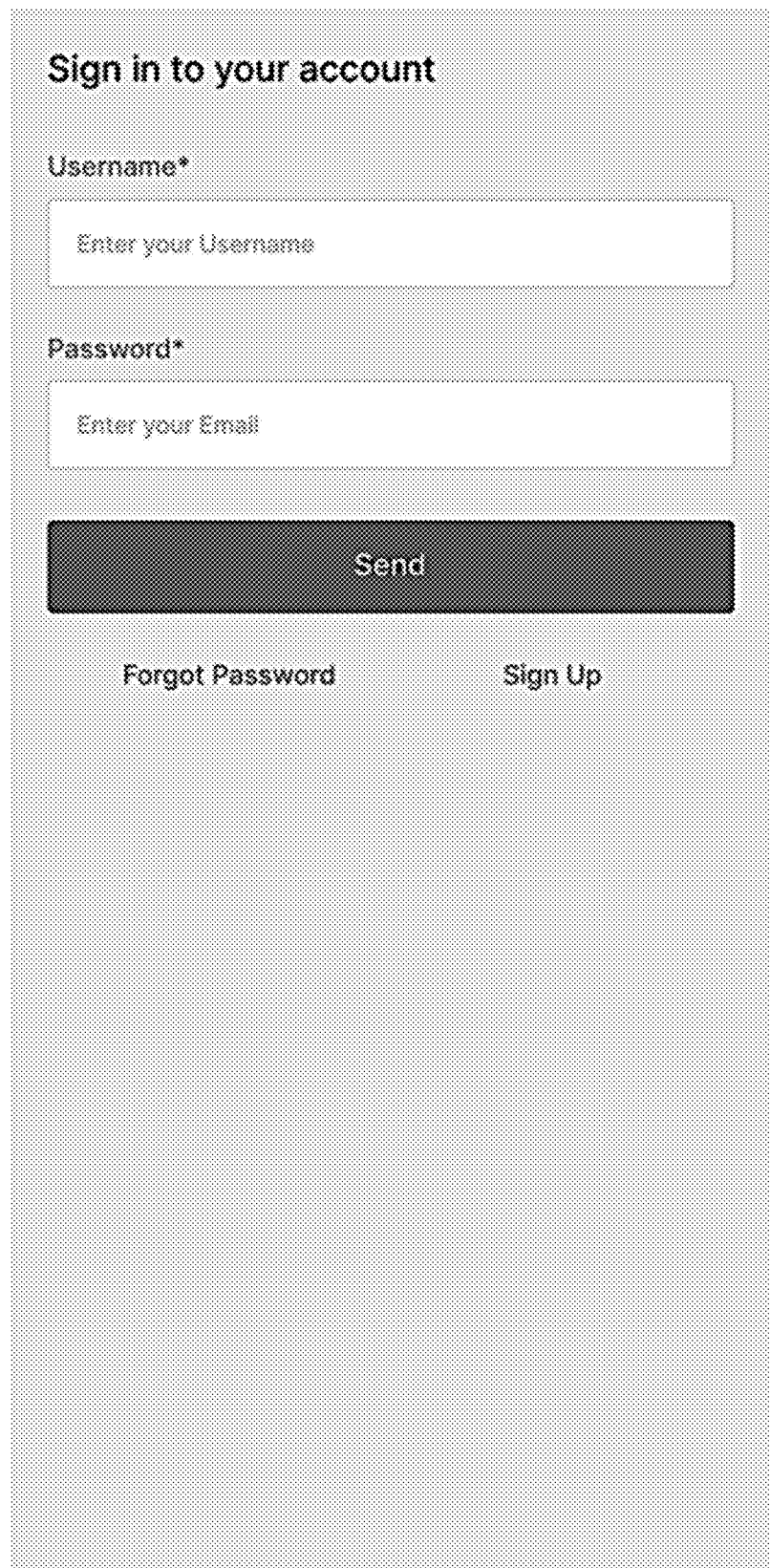

FIG. 11D depicts the sign in screen as accessed on a mobile device. In accordance with the preferred embodiment of the present invention, a user can create a Username and Password in order to access the present invention. This ensures protection of sensitive information and personal data stored within or accessible via the present invention. In some embodiments, two-factor authentication may be implemented to increase security.

Figure 11E:
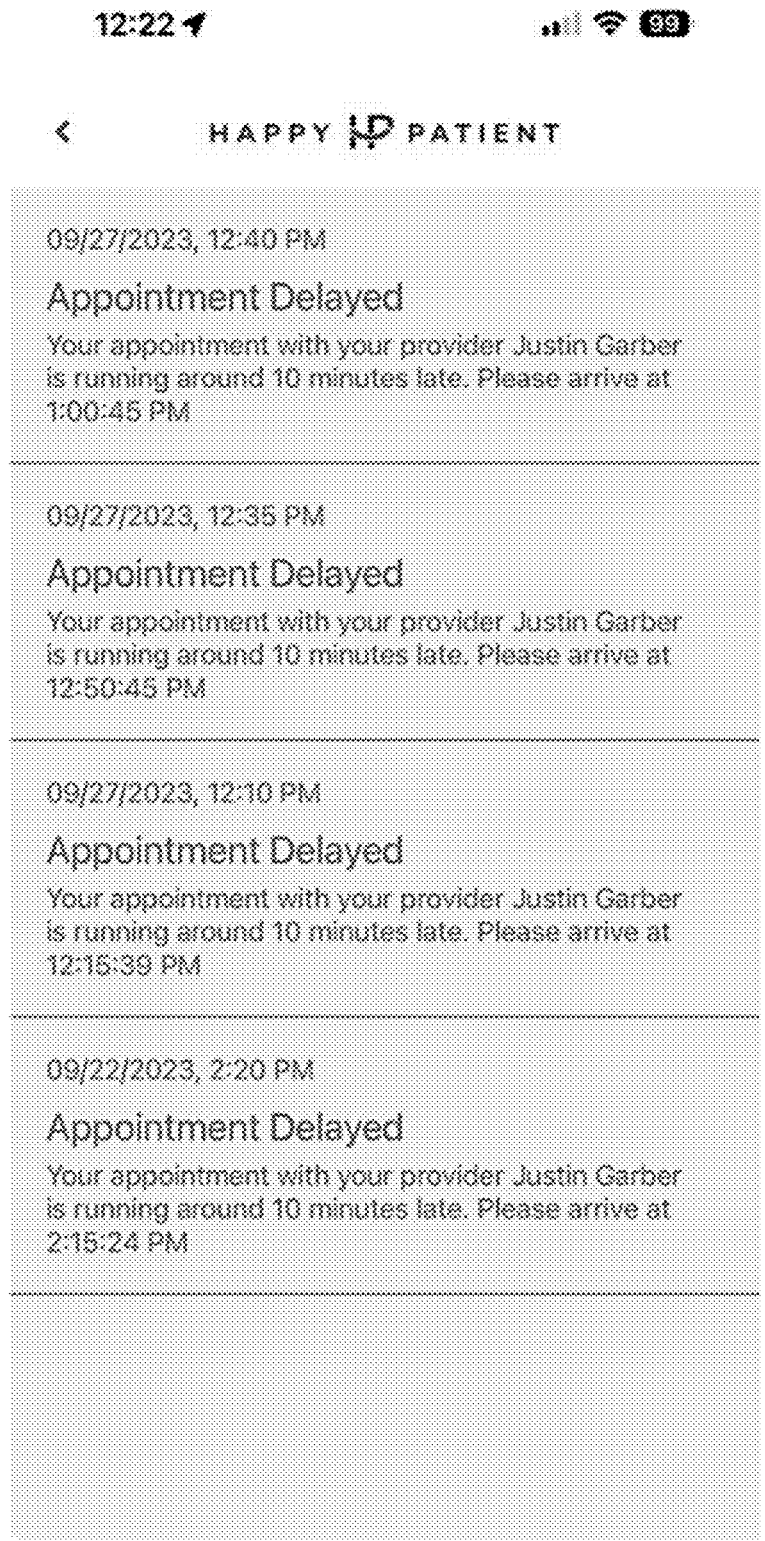

FIG. 11E shows an exemplary notification screen as viewed by a patient on a mobile device. In accordance with the preferred embodiment of the present invention, patients are notified when their scheduled appointment has been delayed. The notification may include information regarding the care provider, the amount of time the appointment is being delayed, and a suggested new arrival time for the patient.

Figure 12A:
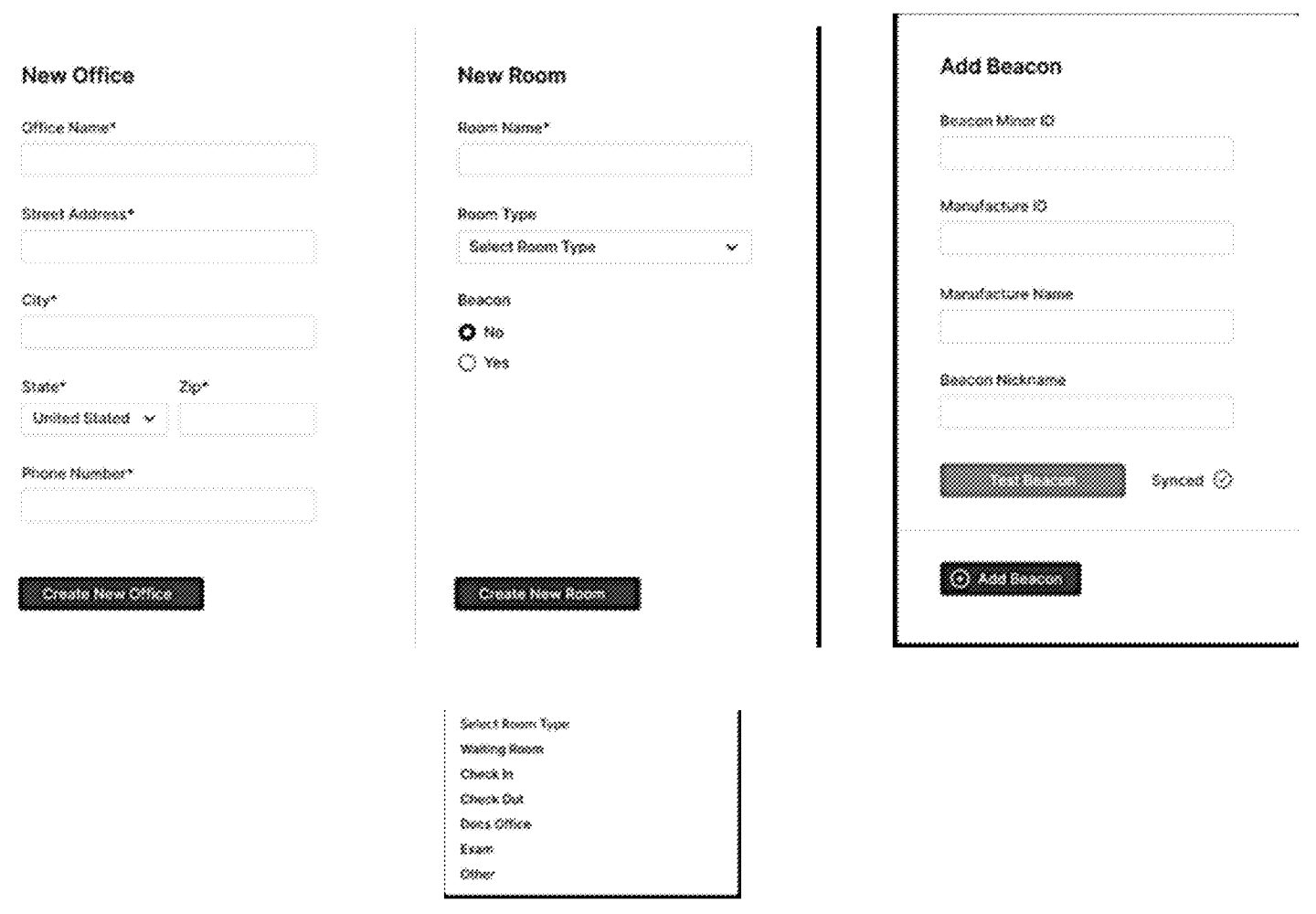

FIGS. 12A-B show the opening screen associated with the present invention and the set-up screen associated with the present invention. FIG. 12A depicts an example screen on which the option to save a new office, new room, or new BLE beacon is presented. A user can also select the room type for the new room for automatic categorization of the new room data.

FIG. 12B shows an exemplary view of the categorical options offered by the present invention. In accordance with the preferred embodiment of the present invention, these categories include, but are not limited to, appointment status type, action level (action needed, follow-up needed, no action needed) patient status type, room status, and room type.

Figure 13:
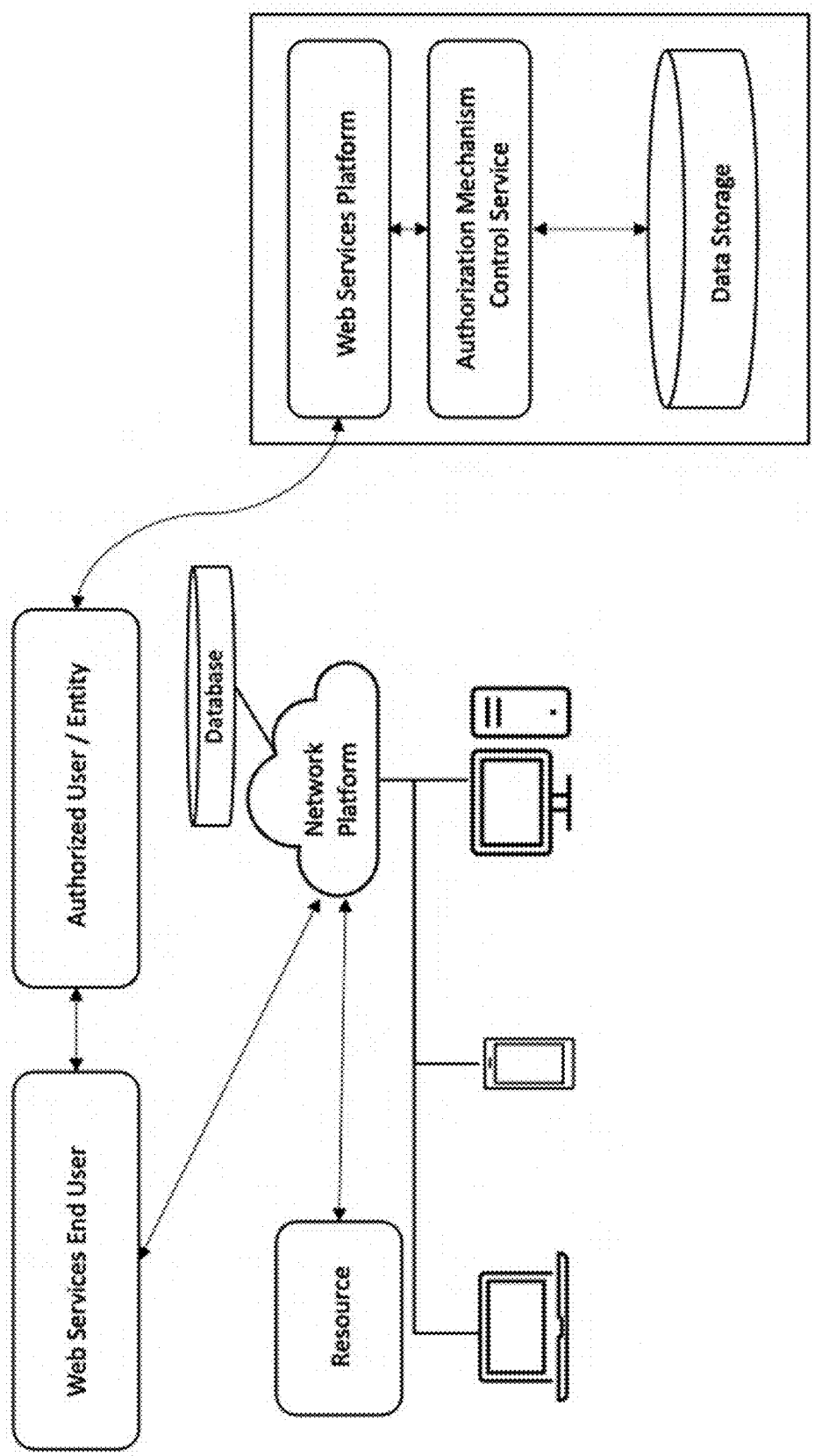
FIG. 13 is a depiction of the platform's web services, as well as the components of an exemplary operating environment in which embodiments of the present invention may be implemented.

FIG. 13 is a diagram showing the web services of the platform and system. The platform and system are all components of an exemplary operating environment in which embodiments of the present invention may be implemented. The system can include one or more user computers, computing devices, or processing devices which can be used to operate a client, such as a dedicated application, web browser, etc. The user computers can be general purpose personal computers (including, merely by way of example, personal computers and/or laptop computers running a standard operating system), cell phones or PDAs (running mobile software and being Internet, e-mail, SMS, Blackberry, or other communication protocol enabled), and/or workstation computers running any of a variety of commercially-available UNIX or UNIX-like operating systems (including without limitation, the variety of GNU/Linux operating systems). These user computers may also have any of a variety of applications, including one or more development systems, database client and/or server applications, and Web browser applications. Alternatively, the user computers may be any other electronic device, such as a thin-client computer, Internet-enabled gaming system, and/or personal messaging device, capable of communicating via a network (e.g., the network described below) and/or displaying and navigating Web pages or other types of electronic documents. Although the exemplary system is shown with four user computers, any number of user computers may be supported.

In most embodiments, the system includes some type of secure network. The secure network can be any type of network familiar to those skilled in the art that can support data communications using any of a variety of commercially available protocols, including without limitation TCP/IP, SNA, IPX, AppleTalk, and the like. Merely by way of example, the network can be a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, GRPS, GSM, UMTS, EDGE, 2G, 2.5G, 3G, 4G, WiMAX, WiFi, CDMA 2000, WCDMA, the Bluetooth protocol known in the art, and/or any other wireless protocol); and/or any combination of these and/or other networks.

The system may also include one or more server computers which can be general purpose computers, specialized server computer (including, merely by way of example, PC servers, UNIX servers, mid-range servers, mainframe computers rack-mounted servers, etc.), server farms, server clusters, or any other appropriate arrangement and/or combination. One or more of the servers may be dedicated to running applications, such as a business application, a Web server, application server, etc. Such servers may be used to process requests from user computers. The applications can also include any number of applications for controlling access to resources of the servers.

The web server can run an operating system including any of those discussed above, as well as any commercially available server operating systems. The Web server can also run any of a variety of server applications and/or mid-tier applications, including HTTP servers, FTP servers, CGI servers, database servers, Java servers, business applications, and the like. The server(s) also may be one or more computers which can be capable of executing programs or scripts in response to the user computers. As one example, a server may execute one or more Web applications. The Web application may be implemented as one or more scripts or programs written in any programming language, such as Java®, C, C#, or C++, and/or any scripting language, such as Perl, Python, or TCL, as well as combinations of any programming/scripting languages. The server(s) may also include database servers, including without limitation those commercially available from Oracle®, Microsoft®, Sybase®, IBM® and the like, which can process requests from database clients running on a user computer.

End users, or users that are viewing and using the network platform, all contribute data to the cloud. A web service platform helps secure that data and maintain the service's functionalities. Only authorized users and entities can authorize or unauthorize content and monitor data stored within the web service. The platform's web services help maintain the operations of elements managed by the computer-readable memory storage unit.

The system may also include one or more databases. The database(s) may reside in a variety of locations. By way of example, a database may reside on a storage medium local to (and/or resident in) one or more of the computers. Alternatively, it may be remote from any or all of the computers, and/or in communication (e.g., via the network) with one or more of these. In a particular set of embodiments, the database may reside in a storage-area network ("SAN") familiar to those skilled in the art. Similarly, any necessary files for performing the functions attributed to the computers may be stored locally on the respective computer and/or remotely, as appropriate. In one set of embodiments, the database may be a relational database, such as Oracle 10g, that is adapted to store, update, and retrieve data in response to SQL-formatted commands.

The present invention allows for redirection to and from a third-party electronic medical record ("EMR") system in order to access patient demographic information and other relevant data related to a patient. This is accomplished via AdvancedMD Integration, or application programming interface ("API") integration with EMR service providers to synchronize scheduled patients and appointments. The present invention may map or store EMR identifiers for location or facility to HP and create and send appointment-related events to a third-party scheduling service.

Figure 14:
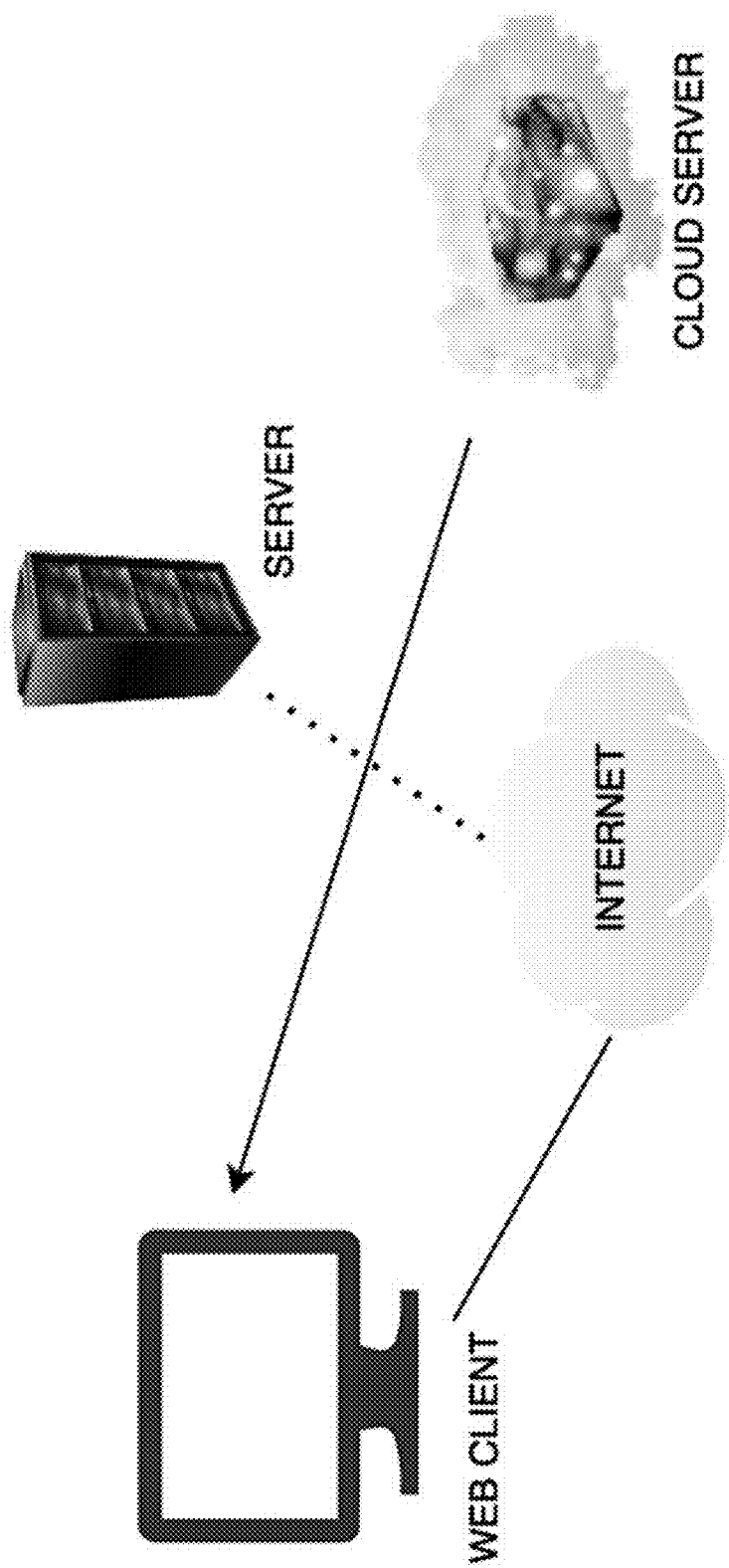
FIG. 14 is a diagram outlining the web services incorporated with server-client communication.

FIG. 14 is a diagram outlining the role of web services in the present invention. In accordance with the preferred embodiment, a web client interacts with the server ecosystem by way of a service connection, such as the internet, which then distributes data and pertinent information such as the web service platform to the cloud server and preliminary servers. This allows for data to be streamlined between the client and the server as well as cloud servers and other database systems. Communication between web services may be completed via Simple Object Access Protocol (SOAP) which allows multiple web service applications to communicate rapidly and efficiently and to provide data to the web client.

The infrastructure of the present invention also allows for the use of web services that enable interaction with and storage of data across devices. Specifically, these web services can allow for the use of cloud software tools and cloud-based data storage. Cloud software tools can be used to allow for increased user authentication and authorization checkpoints for data accessed between parties. The web service software aids in the transmission of data between entities while still maintaining secure access restrictions preventing any unauthorized access to the cloud data.

Figure 15A:
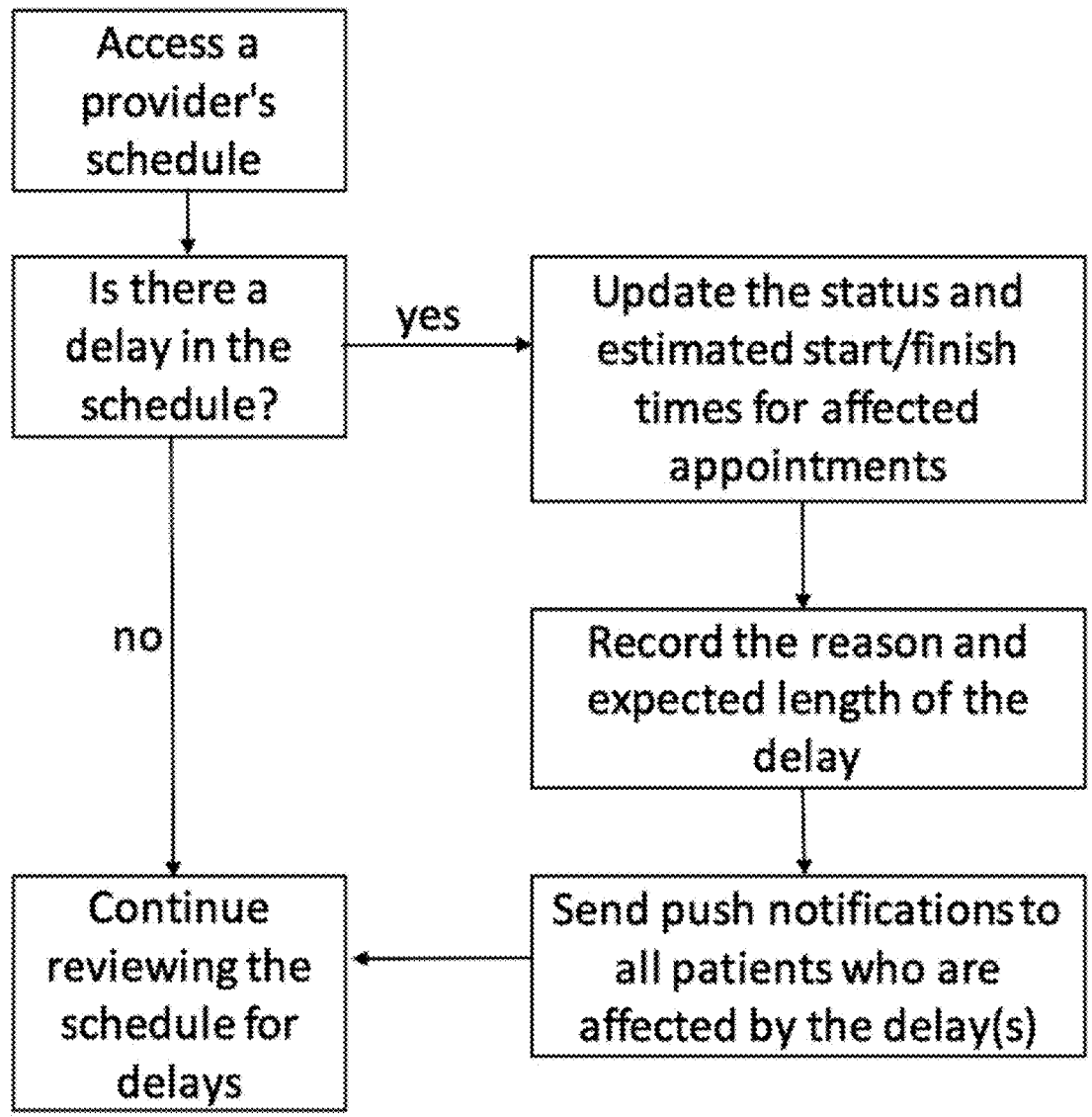
FIGS. 15A-B shows an exemplary flow chart of the algorithm associated with the present invention.
Figure 15B:
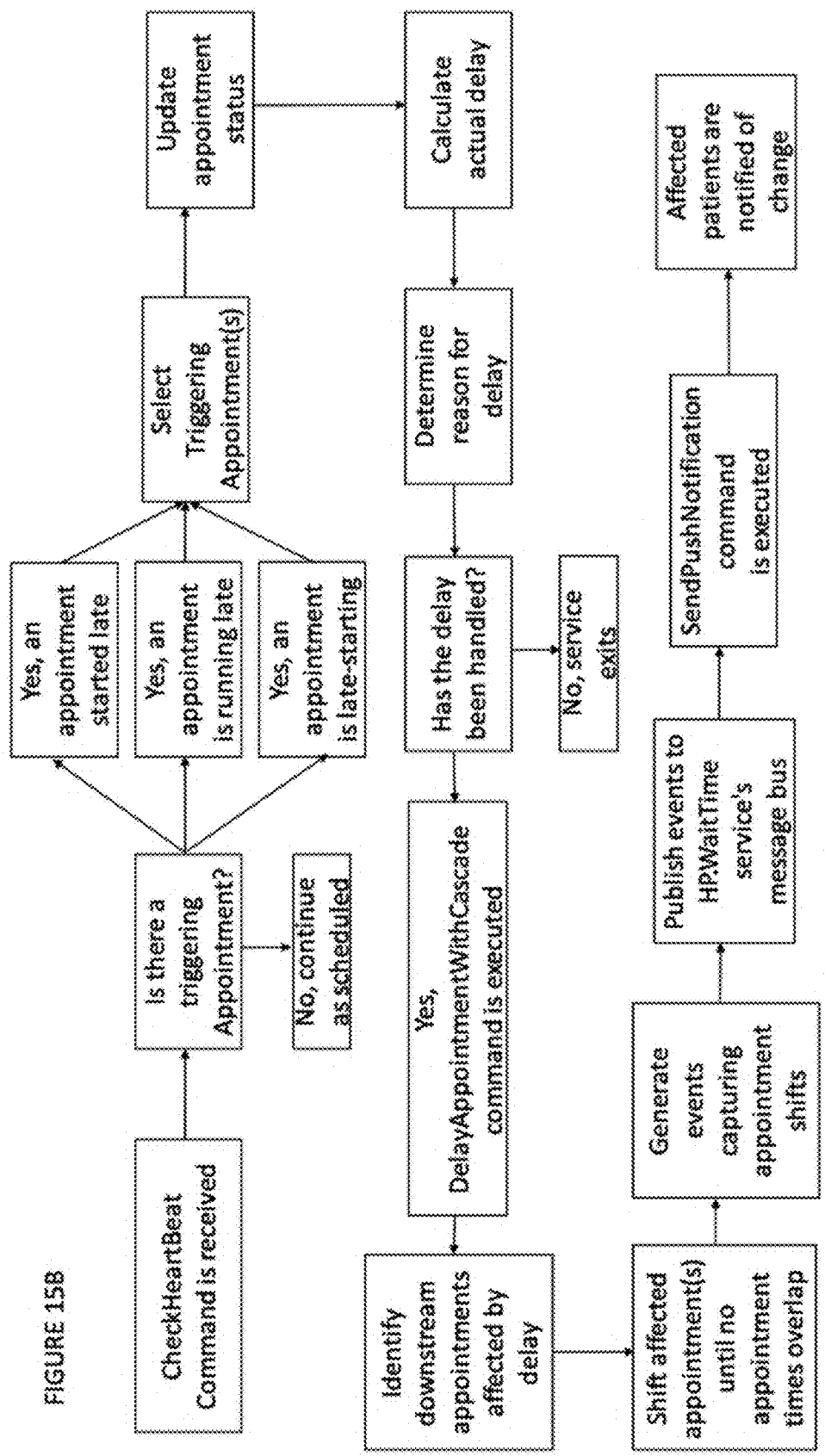

FIGS. 15A-B shows an exemplary flow chart of the machine-learning algorithm (hereinafter referred to as "the algorithm") associated with the present invention. In accordance with the preferred embodiment, the algorithm is used to identify any delays in a provider's schedule. If delays are identified, the algorithm will generate events in order to update the status and estimated start and finish times for the affected appointments, record the reason and expected length of the delay, and send push notifications to all patients who are affected by the delay. The algorithm works by determining if any of the provider's upcoming appointments started late (i.e., they started after their estimated or scheduled start time), are running late (i.e., they have started and are past their estimated finish time), or are late starting (i.e., they have not started and are past their scheduled start time). These appointments are referred to as "Triggering Appointments" as they trigger the algorithm to adjust the schedule for the day accordingly.

The algorithm is implemented and executed by the HP.WaitTime service through the CheckHeartBeat command and handler. When the StartProviderSchedule command is handled by the HP.WaitTime service at the start of the day (or as a chained message when the GreetTheDay command is sent), it schedules a sequence or series of CheckHeartBeat commands to be sent every five minutes (triggered on the five-minute mark). This scheduled sequence of CheckHeartBeat commands is executed for each provider that has an active schedule for the day. When the CheckHeartBeat command is received, the service does the following: retrieve the latest schedule for the provider, search for any Triggering Appointments, select the latest Triggering Appointment, for the Triggering Appointment, the service then: updates the status, calculates the actual delay for the Triggering Appointment, determines the reason for the delay based on the Triggering Appointment's properties (if this delay has already been handled, then the service will exit), and adds a record of the delay to the Triggering Appointment's history.

The service then uses the HappyScheduler scheduling engine to run the command DelayAppointmentWithCascade which identifies downstream appointments that are impacted by the delay and recursively shifts them down the schedule (in its internal state) to accommodate the delay. If a shifted appointment overlaps with the next appointment, then the next appointment is also shifted. This process continues until all downstream appointments are shifted to accommodate the delay. The scheduling engine then returns the set of downstream appointments that can be shifted. Once the set of appointment shifts has been determined and verified, individual events are generated that capture the property and data changes needed for each shifted appointment. The events are then published to the HP. WaitTime service's message bus. In addition, for each affected patient, the service then sends a SendPushNotification command which sends the patient a notification.

The present invention provides the ability to capture, calculate, and store schedule and appointment-related data or events as well as the ability to calculate the estimated wait-time for a provider's scheduled appointments based on in-office provider and patient location tracking. Scheduling microservices are used to store and maintain patient appointment data while logic (services and event-handlers) is used to generate "day-of" appointment events using a combination of individual patient and provider location events. This generates appointment and patient status and events (events include, for example and not by way of limitation, "patient waiting for room," "patient in room alone," "provider with patient (appointment started)"). The present invention implements "expected wait time" algorithms with logic to calculate an estimated wait-time for patient appointments based on scheduled appointment time, actual arrival time, actual appointment start time, and other factors. Patients are also provided the option to not have their location tracked by the present invention. If this option is selected, patients may be alerted to manually input their general location updates, or may be guided to specific locations for check-ins. Furthermore, patients may choose to use nanotag tracking as opposed to using their mobile device.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

What is claimed is:

1. A system for determining a wait time for a user associated with at least one mobile device having a Bluetooth connection, said system comprising:
   at least one Bluetooth-enabled beacon device;
   a first computer server;
   a secure network;
   at least one computer-readable memory storage unit, capable of storing instructions which, when activated by said user, cause said system to:
   detect, via said at least one Bluetooth-enabled beacon device and said at least one mobile device having Bluetooth connection, one or more locations associated with said user by way of receiving a first signal from said at least one Bluetooth-enabled beacon device at said at least one mobile device having Bluetooth connection;
   send a first communication from said at least one mobile device having Bluetooth connection to said first computer server in response to said first signal;
   send a second communication from said first computer server to a second computer server in response to said first signal;
   access, via said secure network, a daily schedule associated with a system administrator;
   compare, via said second computer server, a real-time schedule with said daily schedule associated with said system administrator;
   identify, via said second computer server, inconsistencies between said real-time schedule and said daily schedule;
   adjust, via said second computer server, said daily schedule based on one or more of a stored plurality of daily schedule adjustments and said real-time schedule;
   send a third communication to said first computer server and said at least one mobile device having Bluetooth connection;
   update said stored plurality of daily schedule adjustments in a virtual cloud database;
   monitor signal strength of said at least one Bluetooth-enabled beacon device; and
   adjust settings associated with said at least one Bluetooth-enabled beacon device based on the monitored signal strength of said at least one Bluetooth-enabled beacon device, said settings comprising at least one or more of a minimum number of seconds of receipt of said first signal required for said user to be associated with said location, a minimum number of consecutive pings required for said user to be associated with said location, a weak first signal floor, a maximum first signal ceiling, a number of minutes for ranging timeout, a number of minutes after user checkout to stop tracking said user, and a number of minutes after no ranging to user checkout, where the adjusted settings affect a location resolution algorithm to optimize or minimize Bluetooth-enabled beacon device processing or transmitted data size requirements for Bluetooth ranging code.

2. The system of claim 1, wherein said first communication informs said first computer server of the location of said at least one mobile device having Bluetooth connection, where the location comprises whether and where said at least one mobile device is on a premises.

3. The system of claim 1, wherein said at least one Bluetooth-enabled beacon device tracks the location of said at least one mobile device having Bluetooth connection associated with said user.

4. The system of claim 1, wherein said third communication informs said first computer server and said at least one mobile device having Bluetooth connection of a change to said daily schedule based on said real-time schedule.

5. The system of claim 1, wherein said user is redirected to a third-party virtual calendar interface for cataloging a change to said daily schedule based on said real-time schedule.

6. The system of claim 1, wherein said at least one Bluetooth-enabled beacon device is placed in a specific location.

7. The system of claim 1, wherein a plurality of messages are triggered to send based on a location of said at least one mobile device having Bluetooth connection.

8. The system of claim 1, wherein said plurality of daily schedule adjustments are presented on a virtual dashboard accessible via a user interface accessible via said secure network.

9. A method for determining a wait time for a user associated with at least one mobile device having a Bluetooth connection, said method comprising:
   detecting, via at least one Bluetooth-enabled beacon device and at least one mobile device having Bluetooth connection, a plurality of locations associated with said user by way of
   receiving a first signal from said at least one Bluetooth-enabled beacon device at said at least one mobile device having Bluetooth connection;
   sending a first communication from said at least one mobile device having Bluetooth connection to a first computer server in response to said first signal;
   sending a second communication from said first computer server to a second computer server in response to said first signal;
   accessing, via a secure network, a daily schedule associated with a system administrator;
   comparing, via said second computer server, a real-time schedule with said daily schedule associated with said system administrator;
   identifying, via said second computer server, inconsistencies between said real-time schedule and said daily schedule;
   adjusting, via said second computer server, said daily schedule based on one or more of a stored plurality of daily schedule adjustments and said real-time schedule;
   sending a third communication to said first computer server and said at least one mobile device having Bluetooth connection;
   updating said stored plurality of daily schedule adjustments in a virtual cloud database;
   monitoring signal strength of said at least one Bluetooth-enabled beacon device;
   presenting, on a user interface, a virtual dashboard configured to allow said system administrator to view said plurality of daily schedule changes; and
   adjusting settings associated with said at least one Bluetooth-enabled beacon device based on the monitored signal strength of said at least one Bluetooth-enabled beacon device, said settings comprising at least one or more of a minimum number of seconds of receipt of said first signal required for said user to be associated with one of said plurality of locations, a minimum number of consecutive pings required for said user to be associated with one of said plurality of locations, a weak first signal floor, a maximum first signal ceiling, a number of minutes for ranging timeout, a number of minutes after user checkout to stop tracking said user, and a number of minutes after no ranging to user checkout, where the adjusted settings affect a location resolution algorithm to optimize or minimize Bluetooth-enabled beacon device processing or transmitted data size requirements for Bluetooth ranging code.

10. The method of claim 9, wherein said first communication informs said first computer server of the location of said at least one mobile device having Bluetooth connection, where the location comprises whether and where said at least one mobile device is on a premises.

11. The method of claim 9, wherein said at least one Bluetooth-enabled beacon device tracks the location of said at least one mobile device having Bluetooth connection associated with said user.

12. The method of claim 9, wherein said third communication informs said first computer server and said at least one mobile device having Bluetooth connection of a change to said daily schedule based on said real-time schedule.

13. The method of claim 9, wherein said user is redirected to a third-party virtual calendar interface for cataloging a change to said daily schedule based on said real-time schedule.

14. The method of claim 9, wherein said at least one Bluetooth-enabled beacon device is placed in a specific location.

15. The method of claim 9, wherein a plurality of messages are triggered to send based on a location of said at least one mobile device having Bluetooth connection.

16. The method of claim 9, wherein said method further comprises redirecting, via said secure network, said system administrator to a third-party electronic medical record system for obtaining a medical record associated with said user.

17. A system for determining a wait time for a user associated with at least one mobile device having a Bluetooth connection, said system comprising:
 at least one Bluetooth-enabled beacon device;
 a first computer server;
 a secure network;
 at least one computer-readable memory storage unit, capable of storing instructions which, when activated by said user, cause said system to:
 detect, via said at least one Bluetooth-enabled beacon device and said at least one mobile device having Bluetooth connection, a plurality of locations associated with said user by way of receiving a first signal from said at least one Bluetooth-enabled beacon device at said at least one mobile device having Bluetooth connection;
 send a first communication from said at least one mobile device having Bluetooth connection to said first computer server in response to said first signal;
 send a second communication from said first computer server to a second computer server in response to said first signal;
 access, via said secure network, a daily schedule associated with a system administrator;
 compare, via said second computer server, a real-time schedule with said daily schedule associated with said system administrator;
 identify, via said second computer server, inconsistencies between said real-time schedule and said daily schedule;
 adjust, via said second computer server, said daily schedule based on one or more of a stored plurality of daily schedule adjustments and with said real-time schedule;
 send a third communication to said first computer server and said at least one mobile device having Bluetooth connection;
 update said stored plurality of daily schedule adjustments in a virtual cloud database;
 monitor signal strength of said at least one Bluetooth-enabled beacon device;
 present, via a first user interface on said at least one mobile device having Bluetooth connection, a virtual user dashboard containing information regarding a schedule associated with said user;
 present, via a second user interface on said second computer server, a virtual administration dashboard containing information regarding said plurality of schedule adjustments; and
 redirect, via said secure network, said system administrator to a third-party electronic medical record system for obtaining a medical record associated with said user; and
 adjust settings associated with said at least one Bluetooth-enabled beacon device based on the monitored signal strength of said at least one Bluetooth-enabled beacon device, said settings comprising at least one or more of a minimum number of seconds of receipt of said first signal required for said user to be associated with one of said plurality of locations, a minimum number of consecutive pings required for said user to be associated with one of said plurality of locations, a weak first signal floor, a maximum first signal ceiling, a number of minutes for ranging timeout, a number of minutes after user checkout to stop tracking said user, and a number of minutes after no ranging to user checkout, where the adjusted settings affect a location resolution algorithm to optimize or minimize Bluetooth-enabled beacon device processing or transmitted data size requirements for Bluetooth ranging code.

18. The system of claim 17, wherein said first communication informs said first computer server of the location of said at least one mobile device having Bluetooth connection, where the location comprises whether and where said at least one mobile device is on a premises.

19. The system of claim 17, wherein said at least one Bluetooth-enabled beacon device tracks the location of said at least one mobile device having Bluetooth connection associated with said user.

20. The system of claim 17, wherein said third communication informs said first computer server and said at least one mobile device having Bluetooth connection of a change to said daily schedule based on said real-time schedule.

21. The system of claim 17, wherein said user is redirected to a third-party virtual calendar interface for cataloging a change to said daily schedule based on said real-time schedule.

22. The system of claim 17, wherein said at least one Bluetooth-enabled beacon device is placed in a specific location.

23. The system of claim 17, wherein a plurality of messages are triggered to send based on a location of said at least one mobile device having Bluetooth connection.

* * * * *